US010005825B2

(12) United States Patent
Agadjanyan et al.

(10) Patent No.: US 10,005,825 B2
(45) Date of Patent: Jun. 26, 2018

(54) COMPOSITIONS AND METHODS RELATED TO DISEASES ASSOCIATED WITH DEPOSITS OF AMYLOID, TAU, AND ALPHA-SYNUCLEIN

(71) Applicant: INSTITUTE FOR MOLECULAR MEDCINE, INC., Huntington Beach, CA (US)

(72) Inventors: Michael G. Agadjanyan, Huntington Beach, CA (US); Anahit Ghochikyan, Huntington Beach, CA (US)

(73) Assignee: INSTITUTE FOR MOLECULAR MEDICINE, INC., Huntington Beach, CA (US)

( * ) Notice: Subject to any disclaimer, the term of this patent is extended or adjusted under 35 U.S.C. 154(b) by 0 days. days.

(21) Appl. No.: 14/628,023

(22) Filed: Feb. 20, 2015

(65) Prior Publication Data
US 2015/0232524 A1 Aug. 20, 2015

Related U.S. Application Data

(63) Continuation of application No. PCT/US2013/055877, filed on Aug. 20, 2013.

(60) Provisional application No. 61/691,607, filed on Aug. 21, 2012, provisional application No. 61/792,770, filed on Mar. 15, 2013.

(51) Int. Cl.
C07K 14/47 (2006.01)
C07K 7/08 (2006.01)
A61K 39/00 (2006.01)

(52) U.S. Cl.
CPC ...... *C07K 14/4711* (2013.01); *A61K 39/0007* (2013.01); *C07K 7/08* (2013.01); *C07K 14/47* (2013.01); *A61K 39/00* (2013.01); *A61K 2039/53* (2013.01); *A61K 2039/57* (2013.01); *A61K 2039/575* (2013.01); *A61K 2039/70* (2013.01); *C07K 2319/40* (2013.01)

(58) Field of Classification Search
None
See application file for complete search history.

(56) References Cited

U.S. PATENT DOCUMENTS

2010/0316564 A1   12/2010   Sigurdsson

FOREIGN PATENT DOCUMENTS

| WO | 2001/042306 A2 | 6/2001 |
| WO | 2002/096350 A2 | 12/2002 |
| WO | 2003/015812 A2 | 2/2003 |
| WO | 2009/029272 A2 | 3/2009 |
| WO | 2012/057934 A1 | 5/2012 |

OTHER PUBLICATIONS

Vickers, Drugs Aging, 2002; 19: 487-494.*
Perrin, Nature, 2009; 461: 916-922.*
Hampel et al., Progress in Neurobiology, 2011; 95: 718-728.*
Davtyan et al., Vaccine, 2017; 35: 2015-2024. (Year: 2017).*
Davtyan et al. "The immunological potency and therapeutic potential of a prototype dual vaccine against influenza and Alzheimer's disease." Journal of Translational Medicine, Biomed Central, London GB, 9:127, Aug. 1, 2011.
Palmowski et al. "Competition between CTL narrows the immune response induced by prime-boost vaccination protocols." Journal of Immunology 168: 4391-4398, May 1, 2002.
Skarlas et al., "Influenza virus H5N1 hemagglutinin (HA) T-cell epitope conjugates: design, synthesis and immunogenicity." Journal of Peptide Science, 17(3): 226-232, Mar. 30, 2011.
De Groot et al. "Immunoinformatic comparison of T-cell epitopes contained in novel swine-origin influenza A (H1N1) virus with epitopes in 2008-2009 conventional influenza vaccine." Vaccine, 27(42): 5740-5747, Sep. 25, 2009.
Cribbs, "Abeta DNA vaccination for Alzheimer's disease: focus on disease prevention." CNS & Neurological Disorders, 9(2): 207-216, Apr. 1, 2010.
Davtyan et al. "Immunogenicity, efficacy, safety and mechanism of action of epitope vaccine (Lu AF20513) for Alzheimer's disease: Prelude to a clinical trial." Journal of Neuroscience, 33(11): 4923-4934, Mar. 13, 2013.
Evans et al. "Epitope-based DNA vaccine for Alzheimer's disease: Translational study in macaques." Alzheimer's & Dementia, Jul. 31, 2013. pii: S1552-5260(13)00656-0. doi: 10.1016/j.jalz.2013.04.505.
Ghochiyan et al. "Refinement of a DNA based Alzheimer disease epitope vaccine in rabbits." Human Vaccines & Immunotherapeutics 9(5): 1-9, May 1, 2013.
Troquier et al. "Targeting phospho-Ser422 by active Tau immunotherapy in the thy-Tau22 mouse model: A suitable therapeutic approach." Current Alzheimer Research, 9(4) 397-405, May 1, 2012.
Dagenais et al. T-cell responses to the Trypanosome variant surface glycoprotein are not limited to hypervariable subregions. Infection and Immunity, 77(1): 141-151, Jan. 1, 2009.
Kanaan et al. Phosphorylation in the amino terminus of tau prevents inhibition of anterograde axonal transport. Neurobiology of Aging, 33(4): 826.e15-826.e30, Apr. 1, 2012.
Karin Baraldo, et al.; "N19 Polyepitope as a Carrier for Enhanced Immunogenicity and Protective Efficacy of Meningococcal Conjugate Vaccines"; Infection and Immunity; vol. 72; No. 8; pp. 4884-4887; (Aug. 2004).

(Continued)

Primary Examiner — Christina M Borgeest
(74) Attorney, Agent, or Firm — Roberts Mlotkowski Safran Cole & Calderon, P.C.

(57) ABSTRACT

Disclosed are compositions, comprising one or more immunogens, wherein each immunogen comprises at least two regions, wherein one region comprises at least one amyloid-β (Aβ) B cell epitope or at least one Tau B cell epitope or at least one α-synuclein B cell epitope or combinations thereof, and a second region comprises at least one foreign T helper cell (Th) epitope, and usually multiple foreign Th epitopes. Methods of making and using the compositions are also disclosed.

21 Claims, 21 Drawing Sheets

(56) References Cited

OTHER PUBLICATIONS

Fabiana Falugi, et al.; "Rationally designed strings of promiscuous CD4+ T cell epitopes provide help to Haemophilus influenzae type b oligosaccharide: a model for new conjugate vaccines"; European Journal of Immunology; vol. 31; pp. 3816-3824; (2001).

\* cited by examiner

FIG. 2A

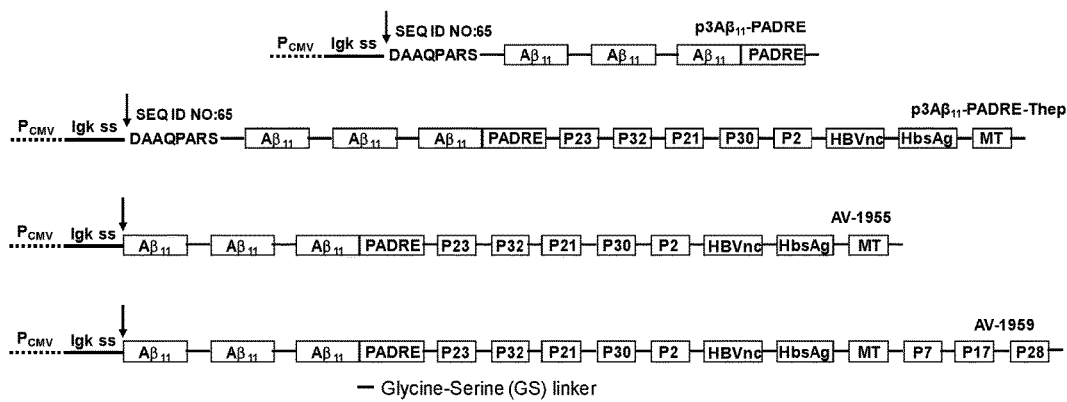

— Glycine-Serine (GS) linker

FIG. 2B

| Th epitope | Origin | aa sequence and position | |
|---|---|---|---|
| PADRE | synthetic | AKFVAAWTLKAAA | SEQ ID NO:36 |
| P23 | Tetanus Toxin | 1084 – VSIDKFRIFCKANPK – 1099 | SEQ ID NO:25 |
| P32 | Tetanus Toxin | 1174 – LKFIIKRYTPNNEIDS – 1189 | SEQ ID NO:26 |
| P21 | Tetanus Toxin | 1064 – IREDNNITLKLDRCNN – 1079 | SEQ ID NO:27 |
| P30 | Tetanus Toxin | 947 – FNNFTVSFWLRVPKVSASHLE – 967 | SEQ ID NO:28 |
| P2 | Tetanus Toxin | 830 – QYIKANSKFIGITE – 843 | SEQ ID NO:29 |
| HBVnc | HBV nuclear capsid | 50 – PHHTALRQAILCWGELMTLA – 69 | SEQ ID NO:33 |
| HBsAg | HBV surface Antigen | 19 – FFLLTRILTIPQSLD – 33 | SEQ ID NO:34 |
| MT | Influenza matrix | 17 – YSGPLKAEIAQRLEDV – 31 | SEQ ID NO:35 |
| P7 | Tetanus Toxin | 506-NYSLDKIIVDYNLQSKITLP-525 | SEQ ID NO:32 |
| P17 | Tetanus Toxin | 586-LINSTKIYSYFPSVISKVNQ-605 | SEQ ID NO:31 |
| P28 | Tetanus Toxin | 674-LEYIPEITLPVIAALSIAES-693 | SEQ ID NO:30 |

|  | Staining with | % of inhibition compared with control | Significance |
|---|---|---|---|
| Dense-core and diffuse plaques | 6E10 Abs | ~89 | P<0.001 |
| Dense-core plaques | ThS | ~86 | P<0.001 |
| Activated microglia | Anti-MHC II Abs | ~81 | P<0.001 |
| Astrocytes | Anti-GFAP Abs | ~71 | P<0.01 |
| Tau pathology | HT-7 Abs (total tau) | ~1-3 | NS |

*In vitro* re-stimulation of PBMCs from NHP immunized with AV-1955 or AV-1959

FIG. 9B

| Monkey # (n=10) | PADRE | P23 | P32 | P21 | P30 | P2 | P7 | P17 | P28 | HBVnc | HBsAg | MT |
|---|---|---|---|---|---|---|---|---|---|---|---|---|
| | | | | | | | | | | Foreign T helper epitopes | | |
| Monkey #1 | + | - | + | + | - | + | - | - | - | - | + | - |
| Monkey #2 | + | - | + | - | - | - | - | + | + | - | - | - |
| Monkey #3 | + | - | + | - | - | - | - | + | + | + | - | - |
| Monkey #4 | + | - | + | + | - | + | - | - | - | + | - | - |
| Monkey #5 | + | + | - | - | + | + | - | + | - | + | - | - |
| Monkey #6 | + | - | + | - | - | - | NA | NA | NA | + | - | + |
| Monkey #7 | + | - | + | - | + | + | NA | NA | NA | - | - | - |
| Monkey #8 | + | + | - | + | + | + | NA | NA | NA | + | - | + |
| Monkey #9 | + | - | - | + | - | - | NA | NA | NA | - | + | - |
| Monkey #10 | + | - | - | - | - | - | NA | NA | NA | - | - | - |
| % of Responders | 100 | 20 | 60 | 50 | 30 | 60 | 0 | 60 | 40 | 50 | 20 | 20 |

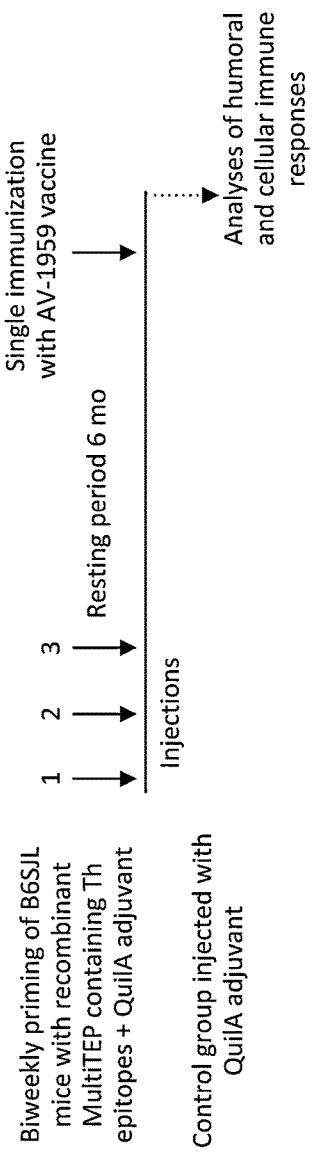
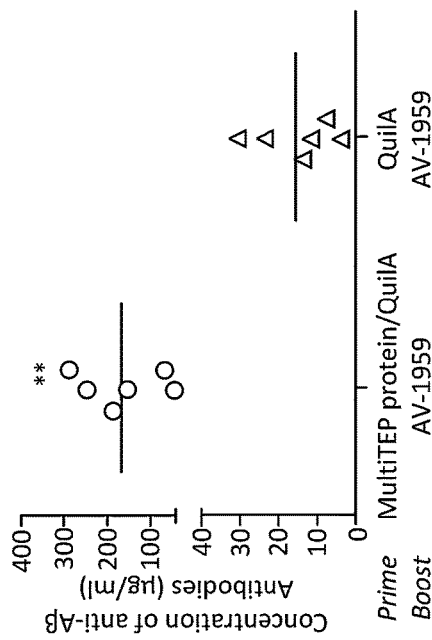
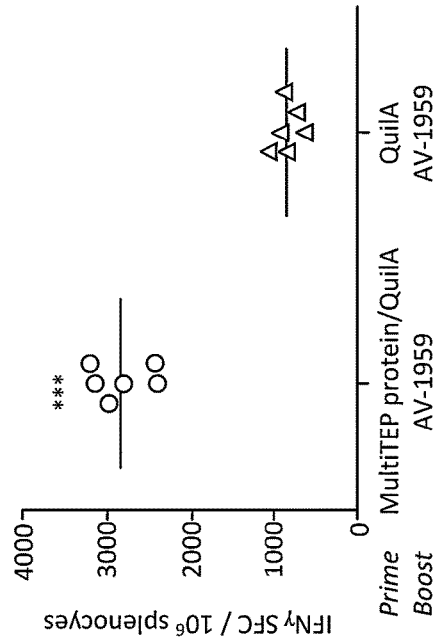

FIG. 11A

Mapping of immunodominant B cell epitopes of α-synuclein in B6SJL mice

| Peptide | Numbers of amino acids | Strength of binding of sera detected by ELISA |
|---|---|---|
| Peptide 1 | 1-20 | - |
| Peptide 2 | 16-35 | - |
| Peptide 3 | 31-50 | + |
| Peptide 4 | 36-69 | +++ |
| Peptide 5 | 61-80 | + |
| Peptide 6 | 76-95 | - |
| Peptide 7 | 91-110 | ++++ |
| Peptide 8 | 106-125 | ++++ |
| Peptide 9 | 121-140 | ++++ |

FIG. 11B

| α-Syn B cell epitope ||
|---|---|
| α-Syn$_{36-69}$ | GVLYVGSKTKEGVVHGVATVAEKTKEQVTNVGGA (SEQ ID NO:46) |
| Foreign T helper cell epitope ||
| MultiTEP Platform ||

| α-Syn$_{36-69}$ | MultiTEP |
|---|---|

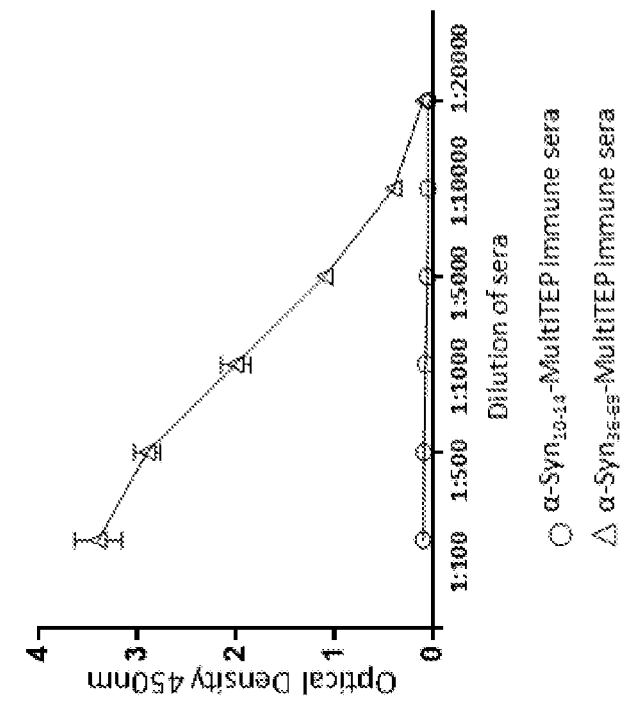

FIG.14

| Peptide | Numbers of amino acids | Strength of binding of sera detected by ELISA |
|---|---|---|
| Peptide 1 | 1-50 | ++++ |
| Peptide 2 | 50-100 | - |
| Peptide 3 | 100-150 | + |
| Peptide 4 | 150-200 | ++ |
| Peptide 5 | 200-250 | ++ |
| Peptide 6 | 250-300 | - |
| Peptide 7 | 300-350 | + |
| Peptide 8 | 350-400 | ++ |
| Peptide 9 | 400-441 | ++ |

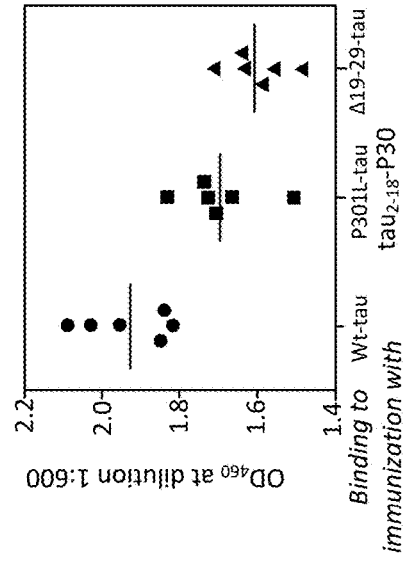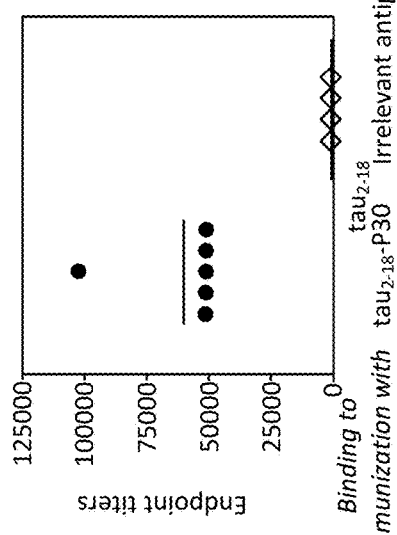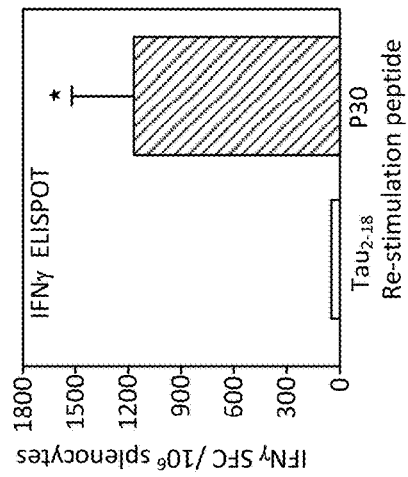
FIG. 15A
FIG. 15B
FIG. 15C ions and methods related to diseases associated with deposits of amyloid, tau, and alpha-synuclein

CROSS-REFERENCE TO RELATED APPLICATIONS

This application is a continuation of International Application PCT/US2013/055877, filed 20 Aug. 2013, which claims priority from U.S. Provisional Applications 61/691,607, filed 21 Aug. 2012 and 61/792,770, filed 15 Mar. 2013, all of which applications are incorporated by reference in their entirety.

STATEMENT REGARDING FEDERALLY SPONSORED RESEARCH OR DEVELOPMENT

Government support was received under R01AG20241, R01NS050895, and R01NS057395 awarded by the National Institutes of Health. The government may have certain rights in the invention

STATEMENT REGARDING SEQUENCE LISTING

The sequence listing associated with this application is provided in text format in lieu of a paper copy, and is hereby incorporated by reference into the specification. The name of the text file containing the sequence listing is 14001-202US_seq-list_ST25.txt; the text file is 21,916 bytes, was created on 19 Feb. 2015, and is being submitted electronically via EFS-web.

FIELD OF THE INVENTION

The present invention relates to compositions and methods for generation of effective vaccine for Alzheimer's disease and other neuropathies.

BACKGROUND

Alzheimer's disease (AD) is the most common form of dementia in the elderly. AD is clinically characterized by progressive loss of memory, behavior impairment and decline of cognitive function. According to the World Health Organization (WHO), approximately 18 million people worldwide have Alzheimer's disease. By 2025, this estimate is projected to grow to 34 million people, with the highest increase expected among developing countries.

Neuropathological features of AD, and other neurodegenerative diseases, include neurofibrillary tangles, deposition of misfolded proteins in plaques and neuronal loss in affected brain regions. These pathological changes result in a profound loss of neurons and synapses over the course of the disease, thereby contributing to a progressive reduction in the functional capacity of the patient.

SUMMARY

The compositions disclosed herein comprise at least one immunogen, wherein each at least one immunogen comprises a region A coupled to a region B; wherein region A comprises at least one amyloid-$\beta$ (A$\beta$) B cell epitope or at least one Tau B cell epitope or at least one $\alpha$-synuclein B cell epitope or a combination of at least one amyloid-$\beta$ (A$\beta$) B cell epitope and at least one Tau B cell epitope or a combination of at least one amyloid-$\beta$ (A$\beta$) B cell epitope and at least one $\alpha$-synuclein B cell epitopes, or a combination of at least one Tau B cell epitope and at least one $\alpha$-synuclein B cell epitope, or a combination of at least one amyloid-$\beta$ (A$\beta$) B cell epitope and at least one Tau B cell epitope and at least one $\alpha$-synuclein B cell epitope, and region B comprises a plurality of foreign T helper cell (Th) epitopes. In another aspect, the composition comprises at least two immunogens, wherein each immunogen is distinct.

In some embodiments, the immunogen comprises a linker domain between region A and region B. In other embodiments, the immunogen comprises linker domains between each epitope. In some embodiments, the order of the regions is A-B and in other embodiments, the order is B-A.

In some embodiments, the compositions further comprise an adjuvant or a pharmaceutical excipient or both.

In another aspect, the composition comprises at least one nucleic acid molecule encoding an immunogen, wherein the immunogen comprises at least one amyloid-$\beta$ (A$\beta$) B cell epitope or at least one Tau B cell epitope or at least one $\alpha$-synuclein B cell epitope or a combination of at least one amyloid-$\beta$ (A$\beta$) B cell epitope and at least one Tau B cell epitope or a combination of at least one amyloid-$\beta$ (A$\beta$) B cell epitope and at least one $\alpha$-synuclein B cell epitopes, or a combination of at least one Tau B cell epitope and at least one $\alpha$-synuclein B cell epitope, or a combination of at least one amyloid-$\beta$ (A$\beta$) B cell epitope and at least one Tau B cell epitopes and at least one $\alpha$-synuclein B cell epitope, and at least one foreign T helper cell (Th) epitope.

The compositions are used to generate an immune response in a subject in need thereof, comprising administering the immunogen to the subject. The subject in need may be at risk of developing or has been diagnosed with Alzheimer's disease or one or more conditions associated with abnormal amyloid deposits, Tau deposits, and $\alpha$-syn deposits. The compositions may be used to prevent, treat or ameliorate a condition associated with deposits of amyloid, tau, and/or $\alpha$-syn, comprising administering to a subject in need thereof an effective amount of the immunogen.

BRIEF DESCRIPTION OF THE DRAWINGS

FIGS. 2A-2B show designs of exemplary vaccines. (FIG. 2A) Schematic representation of constructs encoding various types of epitope vaccines. Parental construct (p3A$\beta_{11}$-PADRE) was modified to express the same three copies of active component, A$\beta_{11}$ B cell epitopes (one epitope with free N-terminal aspartic acid) fused with nine (AV-1955) or twelve (AV-1959) different, promiscuous foreign Th cell epitopes each separated by a neutral spacer with few amino acids (for example, a glycine-serine spacer). Using such constructs one may generate appropriate recombinant proteins. (FIG. 2B) Origin and sequence of various CD4+ T cell epitopes forming the Th epitope strings for AV-1955 and AV-1959 vaccines (designated collectively as the MultiTEP platform).

FIGS. 3A-3B are photographs of Western blots. Correct cleavage of signal sequence and generation of free N-terminus aspartic acid in a first copy of $A\beta_{11}$ in AV-1955 was analyzed in conditioned media (CM) of CHO cells transfected with p3$A\beta_{11}$-PADRE-Thep (Lane 1) and AV-1955 (Lane 2) by IP/WB. Both proteins were immunoprecipitated with 6E10 monoclonal antibodies (Mab) and blots were stained with 6E10 (FIG. 3A) or rabbit antibody specific to the N-terminus of Aβ peptide (FIG. 3B).

FIGS. 4A-4B show results of immunization of mice by gene gun with MultiTEP based AD epitope vaccines AV-1959, AV-1955 and p3$A\beta_{11}$-PADRE. (FIG. 4A) Cellular response measured as IFNγ SFC per $10^6$ splenocytes; (FIG. 4B) Humoral immune responses measured by concentration of anti-Aβ antibodies in μg/mL.

FIGS. 5A-5C show graphs showing results of immunization with MultiTEP based AD epitope vaccine AV-1959. (FIG. 5A) Cellular immune responses are specific to Th epitopes incorporated into the vaccine but not to $A\beta_{40}$, and (FIG. 5B) anti-AO antibodies in mice, rabbits and (FIG. 5C) monkeys.

FIGS. 6A-6C present results of Rhesus macaques vaccinated with MultiTEP based AD epitope vaccine showing therapeutic potency. Anti-Aβ antibody purified from sera of vaccinated monkeys but not irrelevant monkey IgG binds to cortical plaques in AD brain (FIG. 6A) and to immobilized $A\beta_{42}$ monomeric, oligomeric, or fibrillar forms as measured using the Biacore (FIG. 6B). Anti-Aβ antibody inhibits $A\beta_{42}$ fibrils- and oligomer-mediated neurotoxicity (FIG. 6C).

FIGS. 7A-7B show data obtained from APP/Tg mice vaccinated with MultiTEP based AD epitope vaccine. (FIG. 7A) Induced anti-$A\beta_{11}$ antibody significantly reduced diffuse and dense-core Aβ-plaques detected by staining with 6E10 and dense-core plaques detected by staining with ThS, as well as soluble and insoluble Aβ detected by biochemical methods (FIG. 7B).

FIG. 8. shows T cell responses after re-stimulation. Inbred mice of H2b haplotype were vaccinated with MultiTEP based AV-1959 vaccine and restimulated in vitro with different epitopes from the vaccine.

FIGS. 9A-9B show responses of individual, out-bred macaques to different Th cell epitopes after immunization. (FIG. 9A) Mapping of Th cell epitopes in non-inbred macaques with high MHC class II polymorphism. (FIG. 9B) presents the analyses of prevalence of Th epitopes within the NHP population.

FIGS. 10A-10C present a schematic representation of experimental design (FIG. 10A) demonstrating the immunological potential of pre-existing Th cells and results; (FIG. 10B) a cellular response and (FIG. 10C) a humoral response after immunization with multi-TEP protein in QuilA or QuilA alone and boosted with AV-1959.

FIGS. 11A-11B show overlapping peptides of α-syn used for mapping immunodominant B cell epitopes (FIG. 11A). Schematic representation of epitope vaccine based on α-syn B cell epitope fused to MultiTEP platform (FIG. 11B).

FIGS. 12A-12B present data of immune responses in mice vaccinated with an α-Synuclein epitope-based vaccine. (FIG. 12A) Antibody concentration following immunization with α-$Syn_{36-69}$-MultiTEP or irrelevant peptide. (FIG. 12B) Cellular response to MultiTEP and to α-synuclein.

FIGS. 13A-13C show antibody responses to different portions of α-Synuclein. Mice were immunized with epitope vaccine based on $K_{10}AKEG_{14}$ calpain cleavage site of α-Synuclein α-$Syn_{10-14}$-MultiTEP (FIG. 13A). Antibody binding to α-$Syn_{10-18}$ peptide (FIG. 13B) and to full length α-Synuclein protein (FIG. 13C).

FIG. 14 shows results of mapping of immunodominant B cell epitopes in tau protein. Mice were immunized with 4R/2N Tau protein. Binding of generated antibodies to 50-mer peptides comprising tau protein was analyzed by ELISA.

FIGS. 15A-15C present data of immunization of B6SJL mice with $Tau_{2-18}$ fused with a foreign Th cell epitope. (FIG. 15A) Titers of antibody specific to $tau_{2-18}$ peptide were determined in serially diluted individual sera. Lines indicate the average of mice. (FIG. 15B) Binding of anti-Tau2-18 antibodies to wild/type (4R/0N), mutated P301 L and deleted (Δ19-29) tau proteins of 4R/0N isoform (dilution of sera 1:600. Lines indicate the average of $OD_{450}$). (FIG. 15C) Detection of IFN-γ producing cells in the cultures of immune splenocytes activated with P30 peptide and $tau_{2-18}$. The number of IFNγ producing splenocytes was analysed by ELISPOT assay after ex vivo re-stimulation of cells with 10 μg/ml $tau_{2-18}$ and P30 peptides (FIG. 15C). Error bars indicate average±s.d. (P≤0.001).

FIG. 16 presents photographs of immunostaining of brain sections of patients with Alzheimer's Disease (AD) case and normal non-AD case patients. Antibodies include anti-$tau_{2-18}$ sera from mice immunized with $tau_{2-18}$-P30 (left panels), known anti-tau antibodies (middle panels) and control antisera from mice immunized with an irrelevant antigen (Boris) (right panels).

FIGS. 17A-17B present results of antibody blocking brain lysate induction of aggregation of intracellular tau repeat domain (RD). (FIG. 17A) Brain lysate was either untreated or treated with anti-$tau_{2-18}$ antibody and added to HEK293 cells co-transfected with RD(ΔK)-CFP/YFP prior to FRET analysis. Increased FRET signal was detected in wells with untreated brain lysate. Treatment of lysate with anti-$tau_{2-18}$ antibody decreased FRET signal to the baseline level due to blocking the full-length tau in brain lysate and inhibition of induction of RD aggregation. (FIG. 17B) Confocal microscope images of exemplary binding of anti-$tau_{2-18}$ antibody/brain lysate complexes to HEK293 cells transfected with RD-YFP. Secondary anti-mouse immunoglobulin conjugated with Alexa546 was used.

FIGS. 18A-18B present data of anti-$tau_{2-18}$ antibody blocking the trans-cellular propagation of tau RD aggregates. (FIG. 18A) HEK293 cells transfected with RD(LM)-HA were co-cultured for 48 h with an equivalent number of HEK293 cells co-transfected with RD(ΔK)-CFP/YFP prior to FRET analysis. Increased FRET signal was detected in co-cultured cells. Addition of serial dilutions of purified mouse anti-$tau_{2-18}$ or rat anti-$tau_{382-418}$ antibody decreased FRET signal due to inhibition of trans-cellular propagation of aggregated RD. (FIG. 18B) Binding of anti-$tau_{2-18}$ antibodies HEK293 cells transfected with RD(ΔK)-YFP or were mock-transfected (NT) was analyzed by confocal microscope. Anti-$tau_{2-18}$ antibody was added to the culture medium for 48 h. Cells were fixed, permeabilized, and stained with an anti-mouse secondary antibody labeled with Alexa 546 and analyzed by confocal microscopy. Anti-$tau_{2-18}$/RDΔ(K)-YFP complexes were identified when RDΔ(K)-YFP is expressed but not in its absence (NT).

FIG. 19 contains schematics of exemplary multivalent DNA epitope vaccines based on MultiTEP platform. AV-1953 is bivalent epitope composed of 3 copies of $A\beta_{11}$ and 3 copies of $tau_{2-18}$ epitopes fused to MultiTEP platform.

AV-1950 and AV-1978 are trivalent vaccines containing α-syn epitopes KAKEG and α-syn$_{36-69}$, respectively, in addition to Aβ and tau.

Figure 20A:
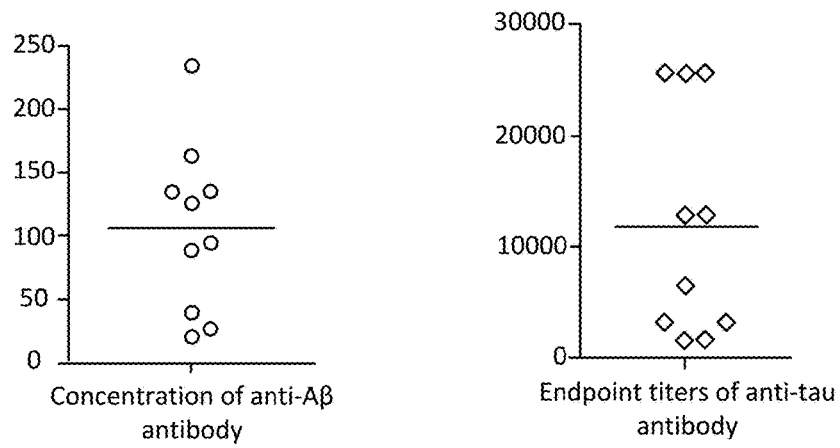
Figure 20B:
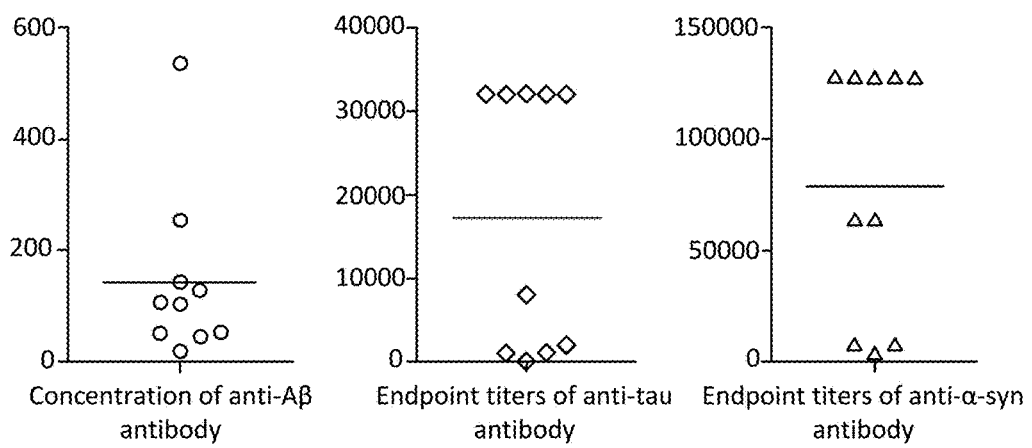
Figure 20C:
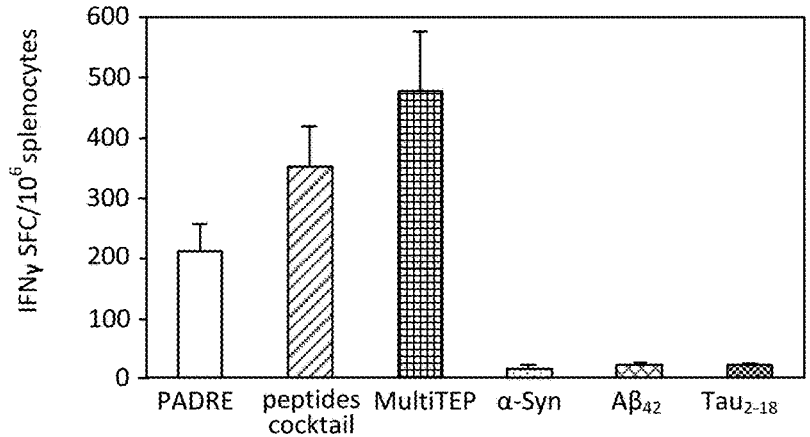

FIGS. 20A-20C show data from immunization of wild-type mice with bivalent and trivalent DNA epitope vaccines. (FIG. 20A) anti-Aβ$_{42}$ and anti-Tau antibody responses generated by bivalent AV-1953 vaccine. (FIG. 20B) anti-Aβ$_{42}$, anti-Tau and anti-α-syn antibody responses generated by AV-1978 trivalent vaccine. Ab responses were measured in sera of individual mice by ELISA and lines represent the average value of Ab. Concentration of Ab specific to α-syn and Aβ$_{42}$ was calculated using a calibration curve generated with mouse anti-α-syn and 6E10 anti-Aβ$_{42}$ antibodies, respectively. Endpoint titers of anti-Tau antibodies were calculated as the reciprocal of the highest sera dilution that gave a reading twice above the cutoff. The cutoff was determined as the titer of pre-immune sera at the same dilution. (FIG. 20C) Trivalent vaccine AV-1978 activated Th cells specific to epitopes of MultiTEP platform but not to B cell epitopes. IFNγ producing cells in the cultures of immune splenocytes were detected by ELISPOT after in vitro re-stimulation of cells with indicated peptides/proteins. Error bars indicate average±s.d. (n=6).

DETAILED DESCRIPTION

A. Immunogenic Compositions

Disclosed herein is compositions of immunogens, wherein the immunogens comprise a region A coupled to a region B. Region A is an active component of vaccine that is responsible for induction of therapeutic antibodies. Region B is a helper component that is responsible for induction of cellular immune responses that help B cells to produce antibodies.

Region A comprises (i) at least one Amyloid-β (Aβ) B cell epitope or (ii) at least one Tau B cell epitope or (iii) at least one α-synuclein (α-syn) B cell epitope or (iv) at least one Amyloid-β (Aβ) B cell epitope and at least one Tau B cell epitope or (v) at least one Amyloid-β (Aβ) B cell epitope and at least one α-synuclein (α-syn) B cell epitope or (vi) at least one Tau B cell epitope and at least one α-synuclein (α-syn) B cell epitope or (vii) at least one Amyloid-β (Aβ) B cell epitope and at least one Tau B cell epitope and at least one α-synuclein (α-syn) B cell epitope. When multiple epitopes are present in Region A, the epitopes may comprise the same epitopic sequence (e.g., multiple copies of Aβ$_{1-11}$) or different epitopic sequences (e.g., Aβ$_{1-11}$ and tau$_{2-13}$). When Region A has different epitopes, the order of the epitopes may be arbitrary or optimized based on in vitro or in vivo tests.

Region B comprises at least one foreign T helper cell (Th) epitope. When multiple T cell epitopes are present in Region B, the epitopes may comprise the same epitopic sequence (e.g., multiple copies of PADRE) or different epitopic sequences (e.g., PADRE and tetanus toxin p23). When Region B has different epitopes, the order of the epitopes may be arbitrary or optimized based on in vitro or in vivo tests.

When two or more immunogens are present in a composition, the immunogens are distinct (i.e., not identical) in region A or region B or both. For the purposes of this disclosure, if two regions contain the same number of epitopes and the same sequence of epitopes, if the arrangement varies then the regions, and hence the immunogens, are distinct. That is, a region comprising epitope 1 and epitope 2 in the order 1-2 is distinct from the order 2-1.

In another aspect, the composition comprises nucleic acid molecules that encode immunogens that comprise a region A coupled to a region B. Region A comprises (i) at least one Amyloid-β (Aβ) B cell epitope or (ii) at least one Tau B cell epitope or (iii) at least one α-synuclein (α-syn) B cell epitope or (iv) at least one Amyloid-β (Aβ) B cell epitope and at least one Tau B cell epitope or (v) at least one Amyloid-β (Aβ) B cell epitope and at least one α-synuclein (α-syn) B cell epitope or (vi) at least one Tau B cell epitope and at least one α-synuclein (α-syn) B cell epitope or at least one Amyloid-β (Aβ) B cell epitope and at least one Tau B cell epitope and at least one α-synuclein (α-syn) B cell epitope. Region B comprises at least one foreign T helper cell (Th) epitope. When multiple epitopes are present in Region A, the epitopes may comprise the same epitopic sequence (e.g., multiple copies of Aβ$_{1-11}$) or different epitopic sequences (e.g., Aβ$_{1-11}$ and tau$_{2-13}$). When Region A has different epitopes, the order of the epitopes may be arbitrary or optimized based on in vitro or in vivo tests.

Region B comprises at least one foreign T helper cell (Th) epitope. When multiple T cell epitopes are present in Region B, the epitopes may comprise the same epitopic sequence (e.g., multiple copies of PADRE) or different epitopic sequences (e.g., PADRE and tetanus toxin p23). When Region B has different epitopes, the order of the epitopes may be arbitrary or optimized based on in vitro or in vivo tests.

When two or more immunogens are encoded, the immunogens are distinct (i.e., not identical) in region A or region B or both. For the purposes of this disclosure, if two regions contain the same number of epitopes and the same sequence of epitopes, if the arrangement varies then the regions, and hence the immunogens, are distinct. That is, a region comprising epitope 1 and epitope 2 in the order 1-2 is distinct from the order 2-1. Multiple immunogens may be encoded by a single nucleic acid molecule or a single immunogen may be encoded by a single nucleic acid molecule. In some embodiments, at least two immunogens are encoded on a single nucleic acid molecule. In other embodiments, each of the immunogens is encoded by separate nucleic acid molecules. In yet other embodiments, more than one immunogen is encoded by a single nucleic acid molecule and at least one other immunogen is encoded by a separate nucleic acid molecule.

The at least one epitope in Region A and Region B can be from 1 to about 18, or from 1 to about 15, or from 1 to about 12, or from 1 to about 9, or from 1 to about 6, or from 1 to about 3, or 1, or 2, or 3, or 4, or 5, or 6, or 7, or 8, or 9, or 10, or 11, or 12 or 13 or 14 or 15 or 16 or 17 or 18 amino acids. When there is more than one epitope, the epitopes may all be different sequences, or some of them may be different sequences.

In some embodiments, the at least one Th epitope of region B is capable of being recognized by one or more antigen-experienced T helper cell populations of a subject. The composition is normally capable of activating a humoral immune response in a subject. In some embodiments, the humoral immune response comprises one or more antibodies specific to pathological forms of Aβ, or Tau, or α-syn proteins.

1. Structure of B Cell Epitopes

A B cell epitope is a peptide comprising a sequence that can stimulate production of antibodies by B cells that bind to the epitope or protein containing the epitope. Moreover, the B cell epitope within the context of this disclosure preferably does not stimulate a T cell response. The B cell epitopes herein may comprise additional sequence, such as amino acids that flank the epitope in the native protein. For example if the minimal sequence of a B cell epitope is amino acids 5-11, a B cell epitope herein may comprise additional amino acids such as residues 3-15. Typical B cell epitopes are from about 5 to about 30 amino acids long.

In some embodiments, the sequence of the at least one Aβ B cell epitope is located within SEQ ID NO: 1, wherein the epitope is less than 42 amino acids long. In some embodiments, the epitope is 15 amino acids in length and in other embodiments, it is less than 15 amino acids in length, i.e., 14, 13, 12, 11, 10, 9, 8, 7, 6, 5, or 4 amino acids. In some embodiments, the epitope comprises the sequence DAEFRH (SEQ ID NO: 7).

In some embodiments, the sequence of at least one Tau B cell epitope is located within SEQ ID NO: 2. Typically, the epitope will be from about 5 to about 30 amino acids long. In some embodiments, the epitope is 12 amino acids in length and in other embodiments, it is less than 12 amino acids in length, i.e., 11, 10, 9, 8, 7, 6, or 5 amino acids. In some embodiments, the epitope comprises the sequence AKAKTDHGAEIVYKSPWSGDTSPRHLSNVSSTGSID (SEQ ID No. 8). In other embodiments, the epitope comprises the sequence RSGYSSPGSPGTPGSRSR (SEQ ID No. 9), or the sequence NATRIPAKTPPAPKTPPSSGEP-PKSGDRSGYSSPGS (SEQ ID No. 10), or the sequence GEPPKSGDRSGYSSPGSPGTPGSRSRTPSLPTPP-TREPKK (SEQ ID No. 11), or the sequence KKVAVVRT-PPKSPSS (SEQ ID No. 12), or the sequence AEPRQEFE-VMEDHAGTY (SEQ ID No. 13). In certain embodiments, the epitope comprises at least 5 contiguous amino acids of SEQ ID NOs. 8-13.

In some embodiments, the sequence of at least one α-syn B cell epitope of region A is located within SEQ ID NO: 3. The epitope will often be between about 5 to 50 amino acids long. In some embodiments, the epitope is about 50 amino acids long; in other embodiments, the epitope is less than about 50 amino acids, in still other embodiments, the epitope is less than about 30 amino acids, or less than about 20 amino acids, or less than about 15 amino acids, or less than about 12 amino acids. In certain embodiments, the fragment comprises the sequence

| | SEQ ID NO: |
|---|---|
| KTKEGVLYVGSKTKEGVVHGVATVAEKTKEQV TNVGGAVVTGVTAVAQK | 14 |
| AGSIAAATGFVKKDQ | 15 |
| QEGILEDMPVDPDNEAYE | 16 |
| EMPSEEGYQDYEPEA | 17 |
| KAKEG | 18 |
| GKTKEGVLYVGSKTKEGVVH | 42 |
| EGVVHGVATVAEKTKEQVTNVGGA | 43 |
| EQVTNVGGAVVTGVTAVAQK | 44 |

In certain embodiments, the epitope comprises at least 5 contiguous amino acids of SEQ ID NOs. 14-18 and 42-44.

In some embodiments, region A comprises a plurality of B cell epitopes. In certain embodiments, region A comprises 1, 2, or 3 B cell epitopes. In other embodiments, region A comprises as many as 18 epitopes, e.g., 1, 2, 3, 4, 5, 6, 7, 8, 9, 10, 11, 12, 13, 14, 15, 16, 17 or 18. The plurality of epitopes can have identical sequences or different sequences. Furthermore, the plurality of epitopes can be all one type—i.e., all having a tau sequence, all having an Aβ sequence, or all having an α-syn sequence. In some embodiments, the plurality of epitopes are from a combination of tau, Aβ, and α-syn. In some embodiments, Region A comprises three Aβ, three tau, and three α-synuclein epitopes. In particular embodiments, the Aβ epitopes comprise residues 1-11, the tau epitopes comprise residues 2-13, and α-synuclein epitopes comprise residues 36-39. In other embodiments, Region comprises three Aβ and three tau epitopes. In particular embodiments, the Aβ epitopes comprise residues 1-11 and the tau epitopes comprise residues 2-13. When region A comprises a plurality of B cell epitopes (or encodes a plurality of B cell epitopes), the epitopes are typically present in a tandem array with linkers between them. The linkers may be of any length and sequence, although short sequences of flexible residues like glycine and serine that allow adjacent protein domains to move freely relative to one another are typically used. Longer linkers may be used in order to ensure that two adjacent domains do not sterically interfere with one another. An exemplary linker sequence is GS (glycine-serine).

In some embodiments, an Aβ B cell epitope may be encoded by a sub-sequence shown in SEQ ID NO:4 or a nucleic acid sequence that encodes the amino acids. Similarly, a Tau B cell epitope may be encoded by the sequence or sub-sequence shown in SEQ ID NO:5, or by a nucleic acid sequence that encodes the same amino acids, or an α-syn B cell epitope may be encoded by the sequence or a sub-sequence shown in SEQ ID NO:6, or by a nucleic acid sequence that encodes the same amino acids.

B cell epitopes of Aβ, tau and α-syn may be identified in a variety of ways, including but not limited to computer program analysis, peptide arrays, phage display libraries, direct binding assays, etc. Computer programs, as well as other tests are commercially or freely available, can be used to predict or directly show B cell epitopes. Candidate sequences can be synthesized and coupled to a carrier protein that is used to immunize an animal, e.g. a mouse. Sera may then be tested by ELISA or other known method for the presence of antibodies to the candidate. In addition, the epitopes may be tested by any method known in the art or described herein for stimulation of T cells.

Suitable epitopes do not stimulate T cells. Some peptides of Aβ are known to act as a T cell epitope. These include the sequences, QKLVFFAEDVGSNKGAIIGLMVGGWIA (SEQ ID NO. 19), VFFAEDVGSNKGAII (SEQ ID NO. 20), QKLVFFAEDVGSNKGAIIGL (SEQ ID NO. 21), LVFFAEDVGSNKGA (SEQ ID NO. 22), QKLVFFAED-VGSNKG (SEQ ID NO. 23), and GSNKGAIIGLMVGG-WIA (SEQ ID NO. 24). Other B cell epitope candidates can be assayed for T cell epitope function using one of the assays described herein or known in the art, such as [$^3$H]thymidine incorporation upon stimulation, MHC-binding assays, intracellular staining, ELISPOT, flow cytometry of CFSE-stained proliferating cells, MTA proliferation assay, that can be used to identify epitope sequences that elicit helper T cell proliferation and thus potentially cause a helper T cell immune responses in subject receiving the composition.

2. T Cell Epitopes (MultiTEP Platform for Vaccines)

The T cell epitopes of the immunogens are "foreign", that is, they are peptide sequences or encode peptide sequences that are not found in the mammals and in the subject to receive the composition. A foreign T cell epitope can be derived from a non-self non-mammalian protein or be an artificial sequence. PADRE is an example of an artificial sequence that serves as a T cell epitope (Alexander et al. Immunity 1:751, 1994; incorporated in its entirety). A "promiscuous T cell epitope" means a peptide sequence that can be recognized by many MHC-II (e.g., human DR) molecules of the immune system and induce changes in immune cells of these individuals such as, but not limited to production of cytokine and chemokines. The T cells specific to these epitopes help B cells, such as B cells specific to amyloid or tau or α-synuclein to produce antibodies to these proteins. It is desirable that antibody produced be detectable and moreover produced at therapeutically relevant titers against pathological forms of these proteins in the sera of vaccinated subjects.

As discussed herein, the T cell epitope should be foreign to the subject receiving the composition. In some embodiments, the at least one Th epitope of one or more of the immunogens is from 12 to 22 amino acids in length. Region B may comprise a plurality of Th epitopes, either all having the same sequence or encoding the same sequence, or a mixture of different Th epitopes. In some embodiments, region B comprises from 1 to 20 epitopes, in other embodiments, region B comprises at least 2 epitopes, in yet other embodiments region B comprises from 2 to about 20 epitopes. Exemplary B regions are illustrated in the Figures and Examples. When region B comprises a plurality of T cell epitopes (or encodes a plurality of T cell epitopes), the epitopes are typically present in a tandem array with linkers between them. The linkers may be of any length and sequence, although short sequences of small amino acids will usually be used. An exemplary linker sequence is GS (glycine-serine). Collectively the string of Th epitopes is called MultiTEP platform.

There are many suitable T cell epitopes. Epitopes can be identified by a variety of well-known techniques, including various T cell proliferation assays as well as using computer algorithms on protein sequences and MHC-binding assays, or chosen from myriad databases, such as MHCBN (hosted at EMBL-EBI), SYFPEITHI (hosted by the Institute for Cell Biology, BMI-Heidelberg and found at (www.syfpeithi.de), IEDB (Vita R, et al. Nucleic Acids Res. 2010 38(Database issue):D854-62. Epub 2009 Nov. 11, and found at www.iedb.org), and SEDB (hosted at Pondicherry University, India, and found at sedb.bicpu.edu.in). T cell epitopes presented by MHC class I molecules are typically peptides between 8 and 11 amino acids in length, whereas MHC class II molecules present longer peptides, typically 13-17 amino acids in length.

In some embodiments, the at least one Th epitope (peptide binding to MHC class II and activating Th cell) is selected from the group consisting of a Tetanus toxin epitope, a diphtheria toxin epitope, a Hepatitis B surface antigen epitope, an influenza virus hemagglutinin epitope, an influenza virus matrix protein epitope, one or more synthetic promiscuous epitopes, or mixtures thereof. For example, suitable Th epitopes include a P23TT Tetanus Toxin epitope comprising the sequence VSIDKFRIFCKANPK (SEQ ID No. 25), a P32TT Tetanus Toxin epitope comprising the sequence LKFIIKRYTPNNEIDS (SEQ ID No. 26), a P21TT Tetanus Toxin epitope comprising the sequence IREDNNTLKLDRCNN (SEQ ID No. 27), a P30TT Tetanus Toxin epitope comprising the sequence FNNFTVSFWL-RVPKVSASHLE (SEQ ID No. 28), a P2TT Tetanus Toxin epitope comprising the sequence QYIKANSKFIGITE (SEQ ID No. 29), a Tetanus Toxin epitope comprising the sequence LEYIPEITLPVIAALSIAES (SEQ ID No. 30), a Tetanus Toxin epitope comprising the sequence LINSTKI-YSYFPSVISKVNQ (SEQ ID No. 31), a Tetanus Toxin epitope comprising the sequence NYSLDKIIVDYN-LQSKITLP (SEQ ID No. 32), a HBV nuclear capsid epitope comprising the sequence PHHTALRQAILCWGELMTLA (SEQ ID No. 33), a HBV surface antigen epitope comprising the sequence FFLLTRILTIPQSLD (SEQ ID No. 34), a MT Influenza matrix epitope comprising the sequence YSGPL-KAEIAQRLEDV (SEQ ID No. 35), a PADRE epitope comprising the sequence AKFVAAWTLKAAA (SEQ ID No. 36) and a PADRE epitope comprising the sequence aK-Cha-VAAWTLKAAa, (SEQ ID NO: 40) where "a" is D alanine and Cha is L-cyclohexylalanine. In some embodiments, the MultiTEP platform is encoded by a nucleic acid molecule.

B. Construction/Preparation of Immunogens

When the immunogens are to be delivered as a DNA composition, the composition will typically be an expression vector. In some embodiments, the vector is capable of autonomous replication. In other embodiments, the vector is a viral vector or a bacterial vector. The vector can alternatively be a plasmid, a phage, a cosmid, a mini-chromosome, or a virus. The sequence encoding an immunogen will be operatively linked to a promoter that is active in host cells. There will typically also be a polyA signal sequence, one or more introns, and optionally other control sequences, such as an enhancer. The promoter can be a constitutive promoter, an inducible promoter, or cell-type specific promoter. Such promoters are well known in the art.

The nucleic acid constructs may also be used to produce a polypeptide immunogen. In this case, the construct(s) are transfected or introduced into host cells in vitro and protein is isolated. Protein may be purified by any of a variety of techniques, including precipitation, affinity chromatography, and HPLC. Suitable host cells include bacteria, yeast cells, insect cells, and vertebrate cells. The choice of a host cell depends at least in part on the backbone of the construct. Affinity tags, such as FLAG and hexa-His may be added to the immunogen to facilitate isolation purification.

Also disclosed herein is a method of making a composition disclosed herein, comprising: obtaining sequence data representing the sequence of the composition; and synthesizing the composition. Resulting proteins may be used without further purification or purified by any of a variety of protein purification methods, including HPLC and affinity chromatography.

C. Coupling of Regions

The A and B regions of the at least two immunogens are coupled. When two or more immunogens are used, the two or more immunogens may also be coupled. Coupling may be through a chemical linkage or peptide linkage (e.g., a fusion protein) or electrostatic interaction (e.g., van der Waals forces) or other type of coupling.

When the linkage is peptidic, the C-terminus of region A may be linked to the N-terminus of region B or vice versa. Alternatively, C-terminus of one B region may be coupled to N-terminus of A region and N-terminus of another B region may be coupled to the C-terminus of the same A region. Moreover, region A may be coupled to region B via a linker domain. Linker domains can be any length, as long as several hundred amino acids, but more typically will be 2-30 amino acids or equivalent length. Linkers are often composed of flexible residues like glycine and serine that allows adjacent protein domains to move freely relative to one another. Longer linkers are used in order to ensure that two adjacent domains do not sterically interfere with one another. Some exemplary linkers include the sequences GS, GSGSG (SEQ ID NO. 37), or YNGK (SEQ ID NO. 38). In some embodiments, one or more of the linkers comprise a helix-forming peptide, such as A(EAAAK)nA (SEQ ID NO. 39), where n is 2, 3, 4, or 5. Alternatively, two immunogens may be synthesized as a multiple antigen peptide (MAP) coupled through 4 or 8 lysine branch.

Chemical cross-linking is an alternative to coupling regions A and B or the at least two immunogens. Linkers and cross-linkers are well-known and commercially available from e.g., Aldrich Co. and ThermoScientific.

D. Formulations and Delivery

The immunogen or immunogens is typically formulated with a pharmaceutically-acceptable excipient. Excipients include normal saline, other salts, buffers, carriers, buffers, stabilizers, binders, preservatives such as thimerosal, surfactants, etc. and the like. Such materials are preferably non-toxic and minimally interfere (or not interfere at all) with the efficacy of the immunogen. The precise nature of the excipient or other material can depend on the route of administration, e.g. oral, intravenous, cutaneous or subcutaneous, nasal, intramuscular, intraperitoneal routes. In some embodiments, compositions are formulated in nano particles and liposomes.

In some embodiments, the composition further comprises an adjuvant. Suitable adjuvants include aluminum salts, such as aluminum hydroxide, aluminum phosphate and aluminum sulfates, saponin adjuvants (e.g. QS-21), 3 De-O-acylated monophosphoryl lipid A (MPL), Montanide, CpG adjuvant, MF59, Inulin-based adjuvant, nanoparticle and liposomal adjuvants. They may be formulated as oil in water emulsions, such as with squalene, or in combination with immune stimulants, such as MPL. Adjuvants can be administered as a component of a therapeutic composition with an active agent or can be administered separately, before, concurrently with, or after administration of the immunogenic therapeutic agent. Other adjuvants include chemokines (e.g. MDC) and cytokines, such as interleukins (IL-1, IL-2, IL4, and IL-12), macrophage colony stimulating factor (M-CSF), tumor necrosis factor (TNF), etc.

The composition can be administered by any suitable delivery route, such as intradermal, mucosal (e.g., intranasal, oral), intramuscular, subcutaneous, sublingual, rectal, vaginal. These and other delivery routes are well known in the art.

The intramuscular (i.m.) route is one such suitable route for the composition. Suitable i.m. delivery devices include a needle and syringe, a needle-free injection device (for example Biojector, Bioject, Oreg. USA), or a pen-injector device, such as those used in self-injections at home to deliver insulin or epinephrine. Intradermal (i.d.) and subcutaneous (s.c.) delivery are other suitable routes. Suitable devices include a syringe and needle, syringe with a short needle, and jet injection devices, etc. The composition may be administered by a mucosal route, e.g., intranasally. Many intranasal delivery devices are available and well known in the art. Spray devices are one such device. Oral administration can be as simple as providing a solution for the subject to swallow.

The composition may be administered at a single site or at multiple sites. If at multiple sites, the route of administration may be the same at each site, e.g., injection in different muscles, or may be different, e.g., injection in a muscle and intranasal spray. Furthermore, it may be administered i.m., s.c., i.d., etc at a single time point or multiple time points. Generally if administered at multiple time points, the time between doses has been determined to improve the immune response.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Compositions comprising nucleic acid may be delivered intramuscularly, intradermally by e.g. electroporation device, intradermally by e.g. gene gun or biojector, by patches or any other delivery system.

Whether it is a polypeptide or nucleic acid that is to be given to an individual, the amount administered is preferably a "therapeutically effective amount" or "prophylactically effective amount". As used herein, "therapeutically effective amount" refers to an amount that is effective to ameliorate a symptom of a disease. A therapeutically effective amount can be a "prophylactically effective amount" as prophylaxis is also therapy. The term "ameliorating" or "ameliorate" is used herein to refer to any therapeutically beneficial result in the treatment of a disease state or symptom of a disease state, such as lessening the severity of disease or symptoms, slowing or halting disease progression, causing a remission, effecting a cure, delaying onset, or effecting fewer or less severe symptoms of a disease when it occurs.

The actual amount administered, and rate and time-course of administration, will depend on the nature and severity of protein aggregation disease being treated. Prescription of treatment, e.g. decisions on dosage is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

The compositions disclosed herein can be administered as sole treatment or provided in combination with other treatments (medical and non-medical), either simultaneously or sequentially dependent upon the condition to be treated.

Also disclosed herein is a method for inducing an immune response in a subject in need thereof, comprising administering a sufficient amount of a composition disclosed herein. The term "sufficient amount" is used herein to mean an amount sufficient to produce a desired effect, e.g., an amount sufficient to modulate protein aggregation in a cell or raise an immune response. The composition may comprise one or more of the immunogens. Additives, such as adjuvants, are optional. Usually, the composition administered is a pharmaceutical composition comprising one or more immunogens. In some aspects, the subject has been diagnosed with Alzheimer's disease or one or more conditions associated with abnormal amyloid deposits, Tau deposits, or α-syn deposits or will be at risk of getting Alzheimer's disease or one or more conditions associated with abnormal amyloid deposits, Tau deposits, or α-syn deposits. An immune response is generated by administration of one of the compositions disclosed herein. An immune response can be verified by assay of T cell stimulation or production of antibodies to the B cell epitope(s). Immunoassays for antibody production are well known and include ELISA, immunoprecipitation, dot blot, flow cytometry, immunostaining and the like. T cell stimulation assays are also well-known and include proliferation assays, cytokine production assays, detection of activation markers by flow cytometry and the like.

Also disclosed herein is a method for treating or ameliorating a condition associated with deposits of amyloid, tau, or α-syn, comprising administering to a subject in need thereof an effective amount of a composition disclosed herein. In general, amelioration can be determined when the total amount of amyloid, Tau protein, or α-syn deposits is decreased post-administration, relative to a control. Other biochemical tests or neuropathology tests can be used, such as determination of ratio of phosphorylated and unphosphorylated tau to $A\beta_{42}$ peptide in CSF, PET-scan with dyes (e.g. Pittsburgh compound B or $^{18}$F-FDDNP) binding to β-Amyloid plaques in brain, less aggregation of the proteins, prevention or slowing of the development of dystrophic neurites, and reduced astrogliosis. Other methods for determining amelioration include cognitive function assays. Amelioration may be manifest as a delay of onset of cognitive dysfunction or memory impairment, a significantly slower rate of decline of cognitive functions and an improvement in the activities of daily living.

Methods for treatment of Aβ, Tau, and α-syn related diseases are also encompassed. β-Amyloid (Aβ), tau, and α-synuclein (α-syn) are the primary components of amyloid plaques (Aβ-plaques), neurofibrillary tangles (NFT), and Lewy bodies (LBs), respectively. Many neurodegenerative disorders are characterized by the presence of one or more of these lesions. For example, Alzheimer's disease (AD) is characterized by the accumulation of Aβ plaques and neurofibrillary tangles. A subtype of AD also displays α-syn-bearing LBs.

Said methods of the invention include administering a therapeutically effective amount of a composition and/or compositions disclosed herein.

The following examples are offered for illustrative purposes only and are not intended to limit the scope of the present invention in any way.

EXAMPLES

Example 1

Design of an Epitope Vaccine

Figure 1:
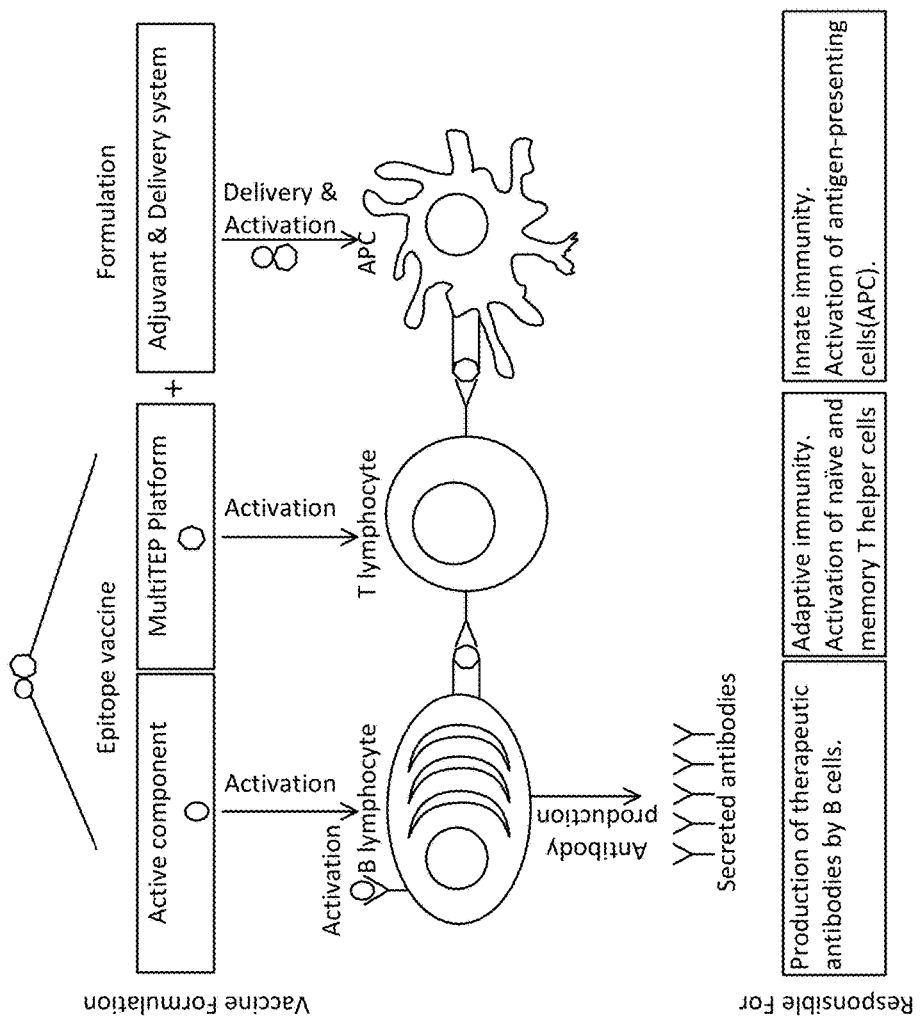
FIG. 1 illustrates the mechanism of action for a epitope vaccine. Adjuvant and delivery systems support the efficient delivery of the vaccine to the immune system. Antigen-presenting cells uptake delivered vaccine and present the antigen to T helper cells specific to Th epitopes incorporated into the vaccine. B cells recognize the active component of the vaccine (B cell epitope) by B cell receptors (first signal for activation) and simultaneously present the Th epitope of the vaccine to the same T helper cells activated by APC creating B cell/T cell synapse. Thus, B cells specific to A$\beta_{11}$ bind the antigen via a B cell receptor (first signal) and get help from activated Th cells (second signal). B cells that are activated in this way begin to produce specific antibodies.

The design of the epitope vaccine compositions is based on a platform of multiple promiscuous T helper (Th) foreign epitopes (MultiTEP). The mechanism of action for MultiTEP-based epitope vaccine is shown in FIG. 1 MultiTEP component of vaccine activates an adaptive immunity providing a broad coverage of human MHC polymorphism and activating both naive T cells and pre-existing memory T cells generated in response to conventional vaccines and/or infections with various pathogens during lifespan. The MultiTEP platform fused with any B cell epitope or combination of epitopes from Aβ, tau, or α-syn induces production of therapeutic antibodies.

Example 2

Figure 3A:
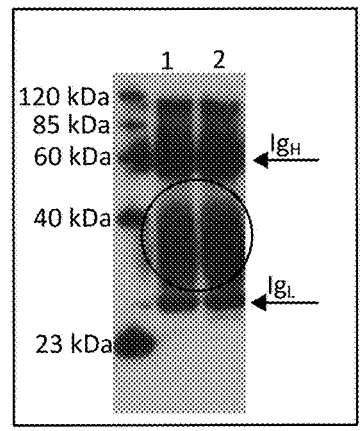
Figure 3B:
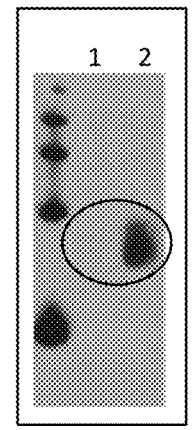

Immunogenicity and Efficacy of DNA-Based MultiTEP Epitope Vaccines in Mice, Rabbits, and Monkeys In this example, modified versions of the $p3A\beta_{11}$-PADRE vaccine are engineered to express $p3A\beta_{11}$ possessing a free N-terminal aspartic acid in the first copy and fused with PADRE and eight (AV-1955) or eleven (AV-1959) additional promiscuous Th epitopes designated collectively as MultiTEP platform. The construction strategy of $p3A\beta_{11}$-PADRE has been described (Movsesyan N, et al. *PLos ONE* 2008 3:e21-4; Movsesyan N, et al. *J Neuroimmunol* 2008 205: 57-63)). A polynucleotide encoding multiple T helper epitopes (MultiTEP) separated by GS linkers is synthesized and ligated to the $3A\beta_{11}$-PADRE minigene (FIG. 2). Correct cleavage of signal sequence and generation of N-terminus aspartic-acid in first copy of $A\beta_{11}$ was shown by IP/WB techniques (FIG. 3).

Figure 4A:
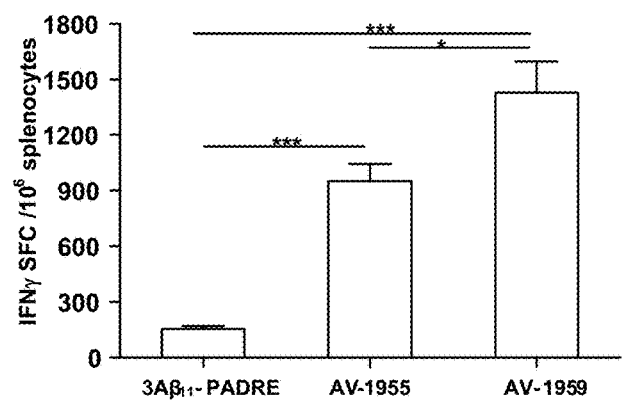
Figure 4B:
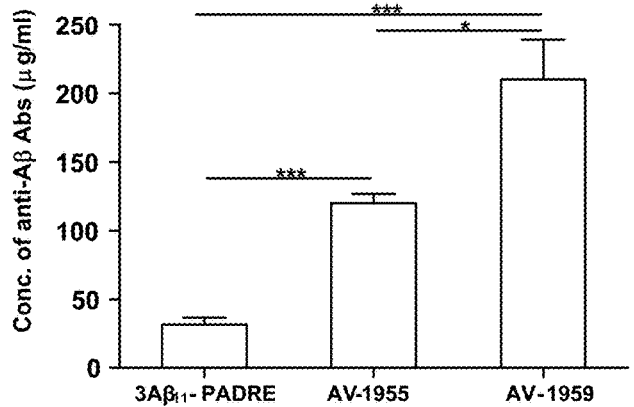

The immunogenicity of MultiTEP-based DNA epitope vaccines is established in mice after delivery by gold particles using a gene-gun device. As shown, cellular (FIG. 4A) and humoral (FIG. 4B) immune responses induced by MultiTEP vaccines AV-1959 and AV-1955 are significantly higher than responses obtained from delivery of a first generation epitope vaccine, which has only PADRE Th epitope.

Immunogenicity of MultiTep vaccines was also tested in mice, rabbits and monkeys after electroporation-mediated needle delivery. Mice, rabbits and monkeys were immunized several times biweekly or by monthly injections of DNA vaccine followed by electroporation. Blood was collected 12-14 d after each immunization. In all tested species, MultiTep DNA vaccine induces strong cellular immune responses specific to foreign Th epitopes (MultiTep platform) but not to $A\beta_{11}$ or $A\beta_{40}$ (data not shown).

Figure 5A:
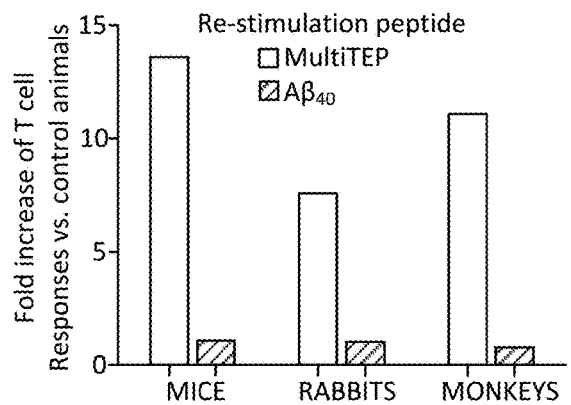

Splenocytes of mice and PBMC of rabbits and monkeys were restimulated in vitro with recombinant protein containing only the Th epitope portion of the vaccine, with a cocktail of individual peptides presenting Th epitopes, or with the $A\beta_{40}$ peptide. Both protein and the peptides cocktail induced equally strong in vitro proliferation and IFNγ production by splenocytes and PBMC of immunized, but not control animals; in contrast, no proliferation or IFNγ production was observed after re-stimulation with $A\beta_{40}$ peptide in splenocytes or PBMC of either immunized or control animals (FIG. 5A and data not shown). The data show that activated Th cells helped B cells to produce high amount of Aβ specific antibodies.

Figure 5B:
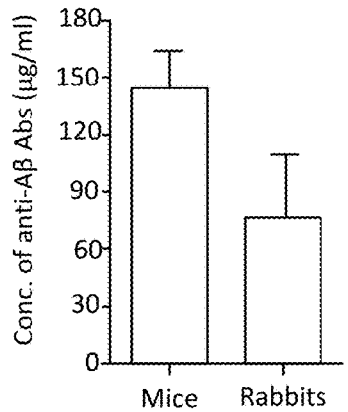
Figure 5C:
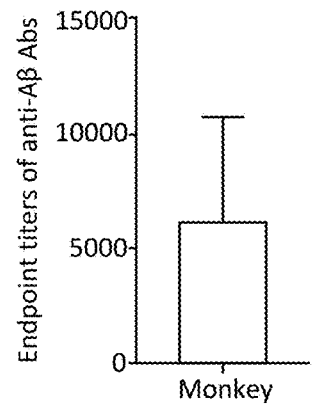

The concentrations (in sera from mice and rabbits) and titers (in sera from monkeys) of anti-Aβ antibodies were determined by standard ELISA. Both MultiTEP platform based DNA vaccines (AV-1955 and AV-1959) induced strong cellular and humoral immune responses in mice (including APP/tg mice, data not shown), rabbits and monkeys. Concentration and endpoint titers of antibodies generated by AV-1959 DNA epitope vaccine are presented in FIG. 5 A,B,C.

Antibodies generated in all species were therapeutically potent. Anti-$A\beta_{11}$ antibodies were purified from sera of mice, rabbits or monkeys immunized with DNA epitope vaccine by an affinity column (SulfoLink, Pierce, Rockford, Ill.) immobilized with Aβ18-C peptide (GenScript, Piscataway, N.J.) as previously described (Mamikonyan G, et al. *J Biol Chem* 282:22376-22386, 2007). Purified antibodies were analyzed via electrophoresis in 10% Bis-Tris gel, and the concentrations were determined using a BCA protein assay kit (Pierce, Rockford, Ill.).

Therapeutic potency of purified antibodies were analyzed in vitro and ex vivo by a neurotoxicity assay (Mamikonyan G, et al. *J Biol Chem* 282:22376-22386, 2007; Ghochikyan A, et al. *Hum Vaccin Immunother* 9:1002-1010, 2013; Davtyan H, et al., *J Neurosci* 33:4923-4934, 2013) and binding to Aβ plaques in human brain tissues. Sera from immunized animals were screened for the ability to bind to human Aβ plaques in 50 µm brain sections of formalin-fixed cortical tissue from an AD case (received from the Brain Bank and Tissue Repository, MIND, UCI, Irvine, Calif.) using standard immunohistochemistry.

Evaluation of Antibodies to Aβ

Binding of antibodies to different forms (e.g., monomeric and aggregated forms) of $A\beta_{42}$ peptide were performed on a BIAcore 3000 SPR platform (GE Healthcare, Piscataway, N.J.) as described (Mamikonyan G, et al. *J Biol Chem* 282:22376-22386, 2007; Ghochikyan A, et al. *Hum Vaccin Immunother* 9:1002-1010, 2013; Davtyan H, et al., *J Neurosci* 33:4923-4934, 2013). Monomeric, oligomeric and fibrillar forms of $A\beta_{42}$ peptides were prepared and immobilized to the surface of biosensor chip CM5 (GE Healthcare, Piscataway, N.J.) via an amine coupling of primary amino groups of the appropriate peptide to carboxyl groups in the dextran matrix of the chip. Serial dilutions of purified anti-$A\beta_{11}$ antibody or irrelevant IgG were injected over each immobilized form of peptide. The kinetics of binding/dissociation was measured as change of the SPR signal (in resonance units (RU)). Data were analyzed with BIAevaluation 4.1.1 software using a 1:1 interaction model to determine apparent binding constants.

Anti-Aβ antibodies generated in different animal models (mice, rabbits and monkeys) vaccinated with MultiTEP-based AD epitope vaccines are shown to be functionally potent. Exemplary data obtained with antibodies isolated from monkey sera are presented in FIG. 6.

Figure 6A:
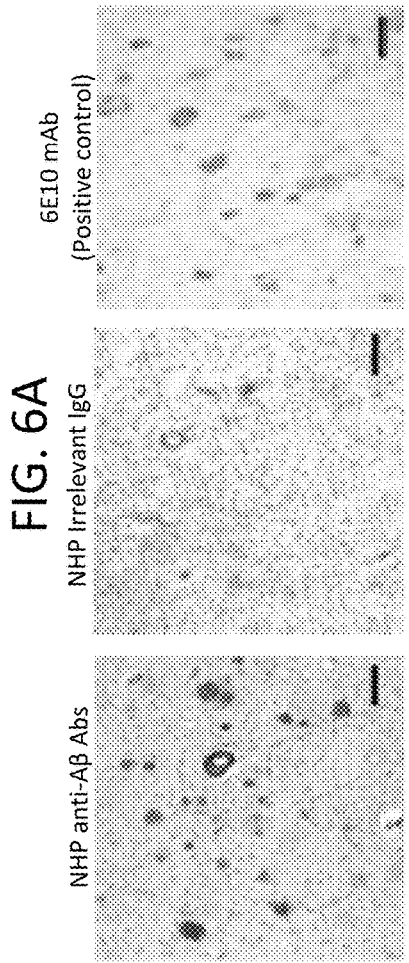
Figure 6B:
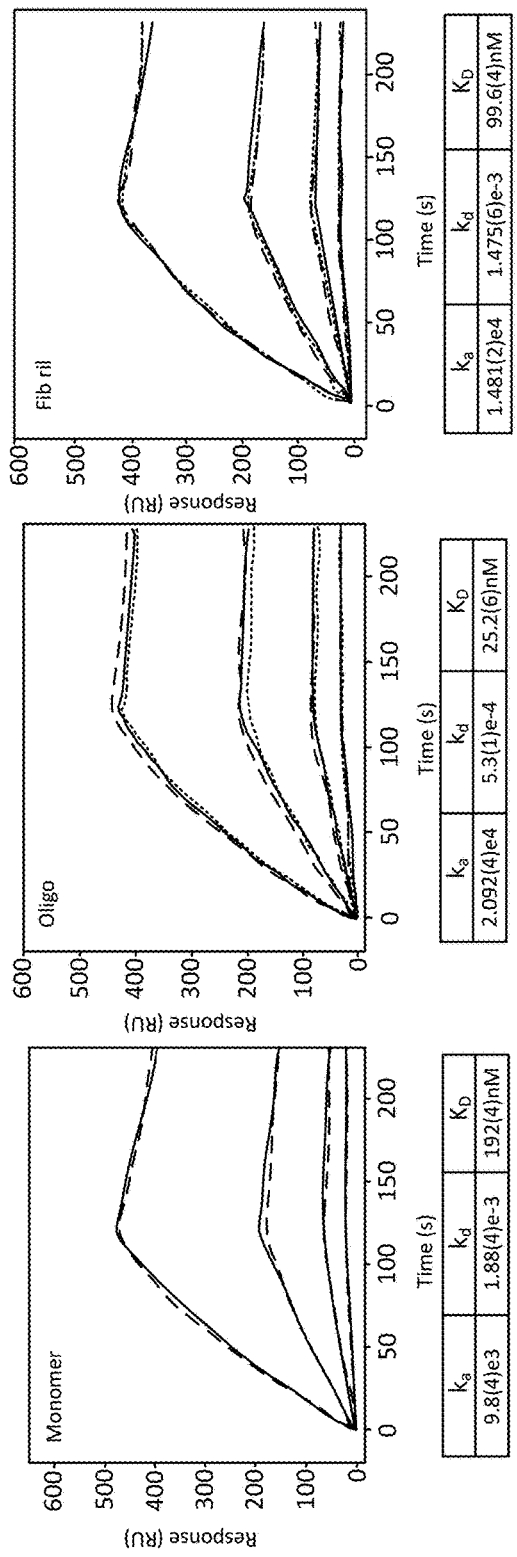
Figure 6C:
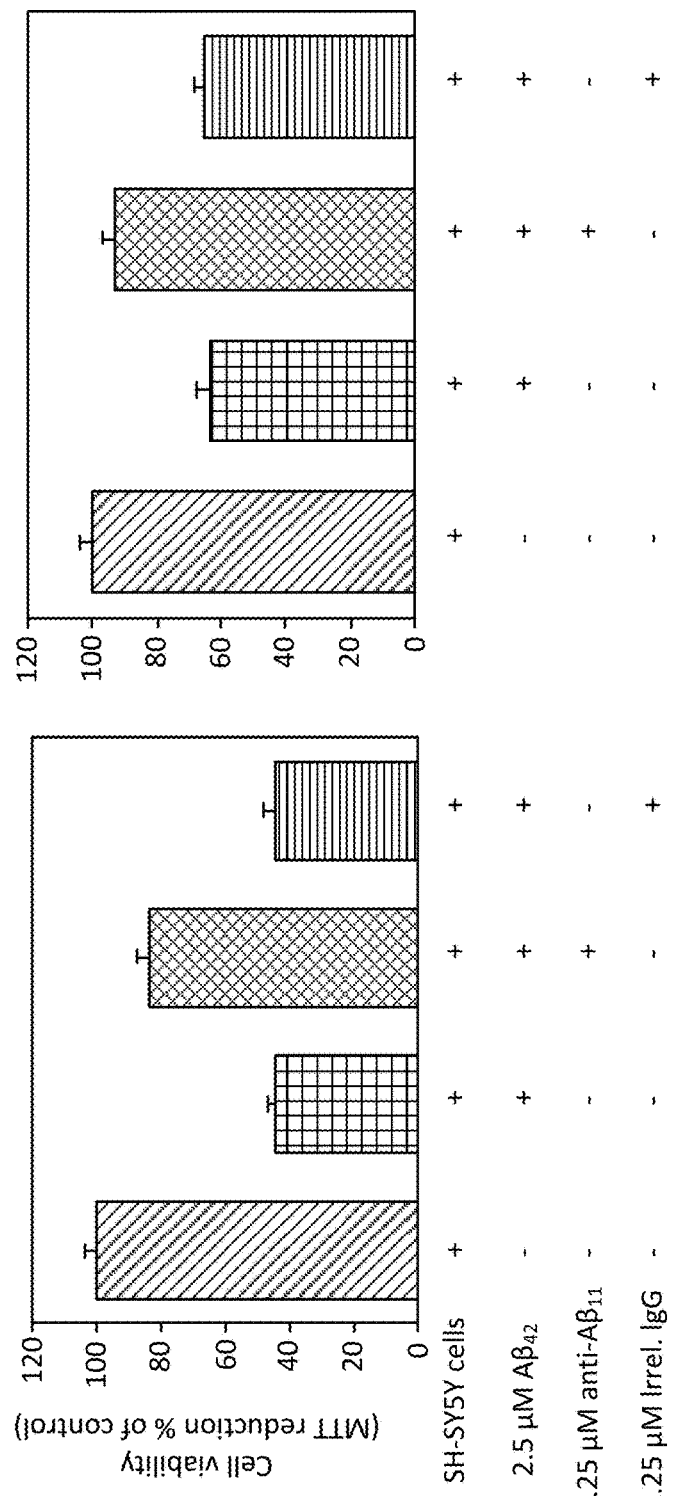

Anti-Aβ antibody purified from sera of rhesus macaques vaccinated with AV-1955, but not irrelevant monkey IgG, binds to immobilized $A\beta_{42}$ monomeric, oligomeric, and fibrillar forms with binding affinity $19.2 \times 10^{-8}$, $2.5 \times 10^{-8}$, $9.9 \times 10^{-8}$, respectively (FIG. 6B) as measured using the Biacore. Anti-Aβ antibody but not irrelevant IgG bound to cortical plaques in brain of AD case (FIG. 6A). Furthermore, anti-Aβ antibody inhibits $A\beta_{42}$ fibrils- and oligomer-mediated neurotoxicity of SH-SY5Y neuroblastoma cell line (FIG. 6C). Similar results were acquired for antibodies obtained from mice and rabbits.

Example 3

In Vivo Therapeutic Efficacy of Antibodies Generated by MultiTEP DNA Epitope Vaccine in 3xTg-AD Mice In this example, the therapeutic efficacy of DNA epitope vaccine was tested in ~4-5 mo old 3×Tg-AD mice (Oddo S; et al. *Neuron* 39:409-21, 2003). Vaccinated mice induced strong cellular response specific to MultiTEP component of vaccine and high production of antibodies specific to $A\beta_{42}$ peptide.

Figures 7A, 7B:
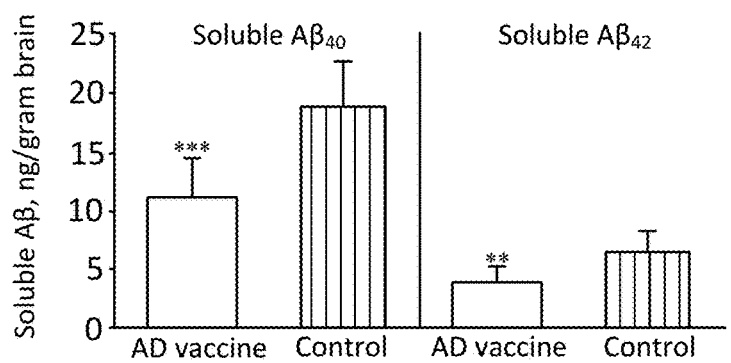

Vaccination prevented neuropathological changes in 18±0.5 mo old immune mice compared with that in control mice. Generated antibodies significantly reduced amyloid burden (diffuse and dense-core plaques) in the brains of immune mice versus control groups (FIG. 7A). Epitope vaccine induced statistically significant reduction of soluble $A\beta_{40}$ and $A\beta_{42}$ ($P<0.001$ and $P<0.01$, respectively) in the brains of immune mice (FIG. 7B). Vaccinated mice developed significantly less inflammation related pathology (microglial activation, astrocytosis) without increasing the incidence of cerebral microhemorrhages in aged 3×Tg-AD mice (FIG. 7A). The reduction of AO deposition was associated with less activation of astrocytosis and MHC class II positive cells. Tau pathology also showed trend toward decrease in vaccinated mice compared with that in control animals (FIG. 7A). No infiltration of T cells into the brains of mice immunized with epitope vaccine was observed.

Example 4

Mapping of T Cell Responses Generated by MultiTEP DNA Epitope Vaccine

This example presents the mapping of immunogenic Th cell epitopes in a MultiTEP platform in mice and monkeys.

Figure 8:
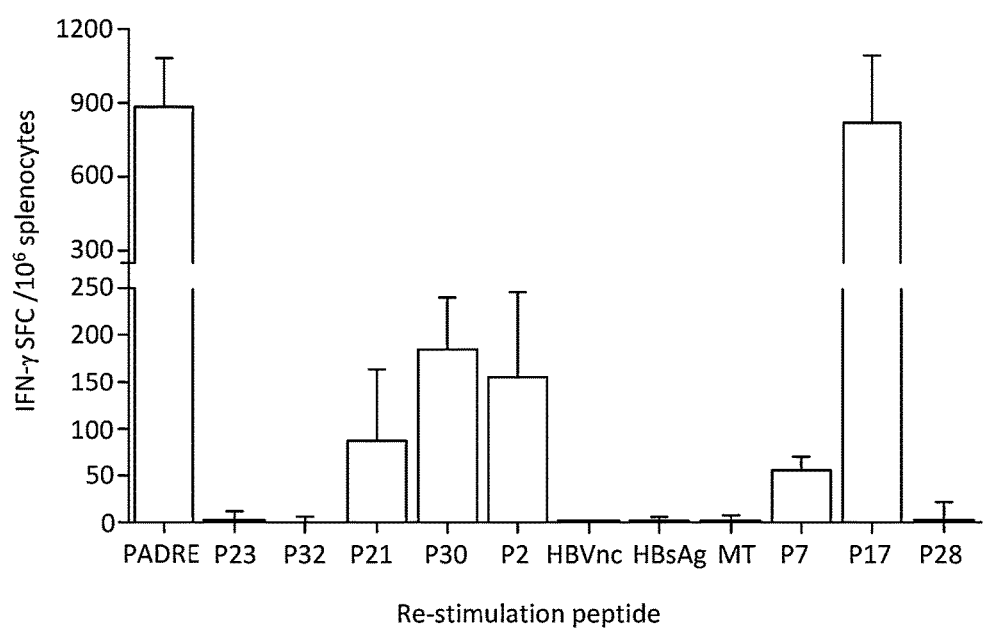

Mice of the H2-b haplotype immunized with MultiTEP based DNA epitope vaccines respond to the epitopes PADRE, P21, P30, P2, P7 and P17 (FIG. 8).

Figure 9A:
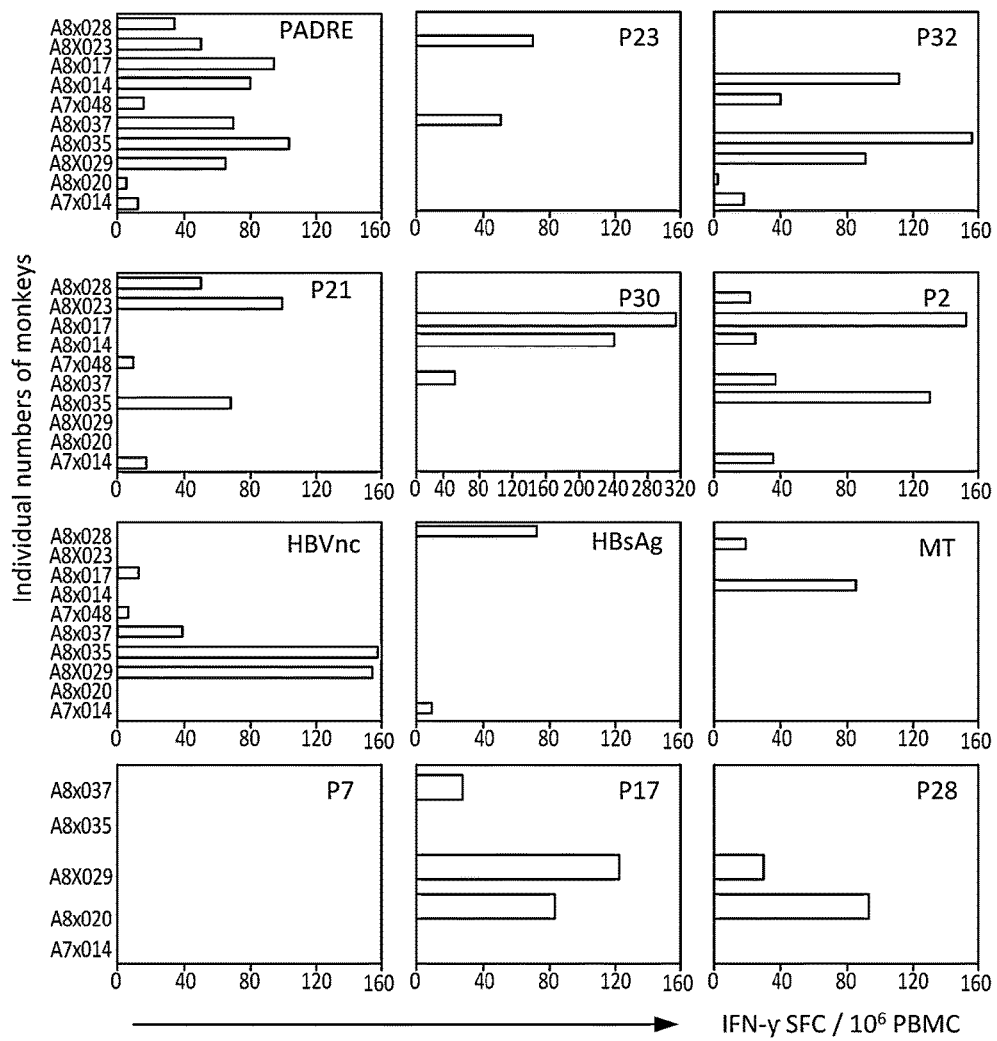

Mapping of Th cell responses in monkeys demonstrated that DNA epitope vaccine AV-1959 induced Th cell responses in all 10 macaques, although the immunogenicity of Th epitopes within the MultiTEP platform varied among individual animals. Quantitative analyses demonstrated that epitopes that are strong in one monkey, can have mediocre or weak immunogenicity in other animals. For example, strong Th cell immune responses (over 100 IFNγ positive SFC per $10^6$ PBMC) were detected in two animals after re-stimulation of immune PBMC cultures with P32, while this response was medium (50-100 IFNγ positive SFC per $10^6$ PBMC) in 1 macaque, weak (less than 50 IFNγ positive SFC per $10^6$ PBMC) in 3 macaques, and no response was detected in 4 animals (FIG. 9A).

The Table in FIG. 9B presents the analyses of prevalence of Th epitopes within the NHP (non-human primate) population used in the vaccination study. The data demonstrate that each macaque with diverse MHC class II molecules responded to a different set of Th epitopes. For example, PADRE is immunogenic in 100% of macaques: PBMC from all animals responded to the re-stimulation with the synthetic promiscuous Th epitope, PADRE, which is known to be recognized by 14 of 15 human DR molecules (Alexander J, et al. *Immunity* 1:751-761, 1994). Next more prevalent Th epitopes are P2, P32, P17, P21 from TT and HBVnc from HBV that are immunogenic in 50-60% of vaccinated animals. The remaining Th epitopes were capable of activating Th cells in 20-30% of animals, while one Th epitope, P7 is not recognized by any of the 5 macaques immunized with AV-1959 vaccine.

Example 5

MultiTEP Epitope Vaccine Activates Memory Th Cells Specific to Foreign Epitopes

An advantage of the epitope vaccine design is overcoming the phenomenon of immunosenescence in elderly individuals by activating pre-existing memory Th cells. In this example, we immunized mice with recombinant protein based MultiTEP epitope vaccine. Previously, the immunogenicity and the therapeutic efficacy of the first generation peptide- and recombinant protein-based vaccines in Tg2576 mice, an APP over-expressing model of AD (Hsiao K, et al.

Science 1996, 274:99-102), was reported (Petrushina I, *J Neurosci* 2007, 27:12721-12731; Davtyan H, et al., *J Neurosci* 2013, 33:4923-4934).

As shown herein, recombinant protein-based MultiTEP vaccine is able to induce stronger immune responses in mice possessing pre-existing memory Th cells. Two groups of B6SJL mice were immunized with recombinant protein containing only the MultiTEP component of AV-1959 vaccine formulated in QuilA, or QuilA only (FIG. 10A). After a 6-month resting period, MultiTEP-primed mice and control mice were boosted with the recombinant protein-based AV-1959 epitope vaccine and both cellular and humoral immune responses were analyzed (FIG. 10B, C). Boosting of MultiTEP-primed mice with AV-1959 induced strong Th cell responses specific to MultiTEP protein: very large number of cells producing IFNγ was detected in this group of mice with pre-existing memory Th cells vs control mice (FIG. 10B). Moreover, the single injection with AV-1959 vaccine formulated in the strong Th1 adjuvant Quil A led to induction of a strong anti-Aβ antibody response only in mice with pre-existing memory Th cells: concentrations of anti-Aβ antibodies were significantly higher ($P \leq 0.001$) than that in control mice (FIG. 10C). These results demonstrate that even a single immunization with epitope vaccine strongly activated pre-existing memory CD4$^+$T cells specific to the Th epitopes of this vaccine and rapidly led to the robust production of antibodies specific to the B cell epitope of the same vaccine.

Importantly, activation of pre-existing memory T cells and rapid production of high concentrations of anti-Aβ antibodies had a therapeutic effect and led to delay of cognitive impairment and the accumulation of pathological Aβ in Tg2576 mice.

Two groups of 5 mo old mice were injected with either MultiTEP protein formulated in QuilA or QuilA only (control) 3 times bi-weekly. Six months after the last injection, at the age of 11 mo, mice were boosted monthly with protein-based AV-1959 epitope vaccine formulated in QuilA until they reached the age of 16 mos. Control mice were injected with QuilA only. After a single boost with epitope vaccine, a strong anti-Aβ antibody response was detected in mice with pre-existing memory Th cells. Concentrations of anti-Aβ antibodies in these mice were significantly higher (P0.001) than that in mice primed with QuilA only, and boosted with vaccine (32.20±10.55 μg/ml vs 0.82±0.24 μg/ml, respectively). After boosts the antibody responses reached to the equal level in both groups (data not shown).

The effect of vaccination on delay of cognitive impairment in mice was tested by "Novel Object Recognition" test. Each mouse was habituated to an empty arena for 5 min one day prior to testing. On the first day of testing, mice were exposed to two identical objects placed at opposite ends of the arena for 5 minutes. Twenty-four hours later, the mouse was returned to the arena, this time with one familiar object and one novel object. Time spent exploring the objects was recorded for 5 minutes. The recognition index represents the percentage of the time that mice spend exploring the novel object. Objects used in this task were carefully selected to prevent preference or phobic behavior. Although both experimental groups showed improved behavior, only mice with pre-existing memory T cells achieved a recognition index significantly higher than control mice (data not shown). Thus, although mice from both groups had an equal level of antibodies at the time of behavior testing, more rapid generation of high concentrations of anti-Aβ antibodies in mice with pre-existing memory T cells at the start of boosting was more beneficial to the mice. The improvement in cognitive function was associated with less profound neuropathological changes in brains of mice with pre-existing memory Th cells compared with both control non-immunized mice or mice without pre-existing memory Th cells at the time of boosting injection.

Example 6

Epitope Vaccine Targeting Alpha-Synuclein

This example demonstrates that an α-syn-based epitope vaccine induces strong anti-α-syn antibody response without generating cellular immune responses specific to this self molecule.

Figure 12A:
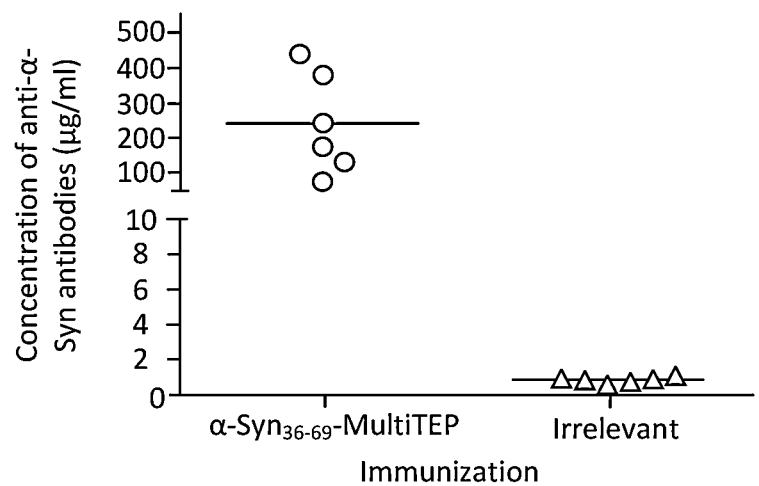
Figure 12B:
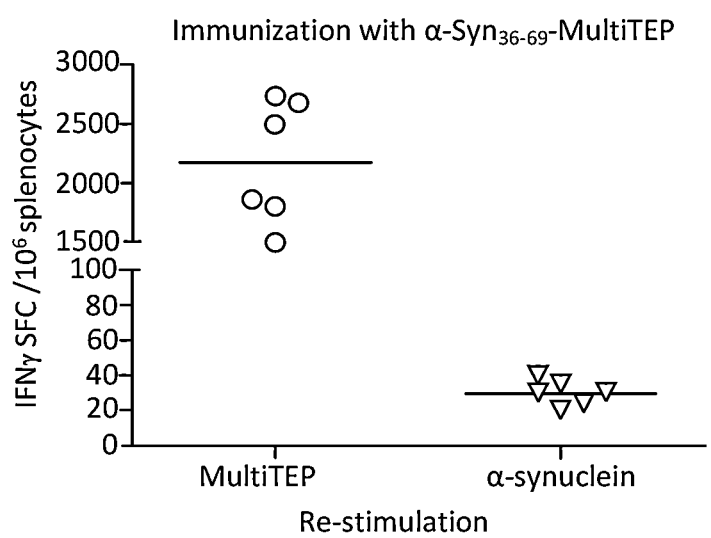

To identify immunodominant B cell epitopes of α-synuclein, mice were immunized with DNA encoding full-length α-synuclein fused with promiscuous strong Th cell epitope PADRE. Sera from vaccinated mice, collected after the third immunization were used for mapping of B-cell epitopes using 9 overlapping 20-mer peptides constituting α-syn protein. Antibodies specific to six different peptides were detected (FIG. 11A). Three of six B-cell epitopes that are localized at the C-end region of α-syn coincide with the epitopes previously detected (Masliah E, et al. *Neuron* 46:857-868, 2005). Selected peptides were tested for whether they possess a Th cell epitope (data not shown). Epitope 36-69 was selected for generation of epitope vaccine. Recombinant protein composed of α-syn$_{36-69}$ attached to MultiTEP platform (FIG. 11B) purified from *E. coli*. B6SJL mice were immunized with this immunogen formulated in QuilA adjuvant. Both B and T cell responses were analyzed after three bi-weekly immunizations. Control animals were injected with adjuvant only. α-syn$_{36-69}$-MultiTEP induced strong antibody responses specific to the appropriate peptide (data not shown) and full-length human α-syn (FIG. 12A). Cellular immune responses were measured by ELISPOT (FIG. 12B). Mice immunized with α-syn$_{36-69}$-MultiTEP induced robust T cell responses after re-stimulation with MultiTEP protein, but not with full-length α-synuclein protein (FIG. 12B) or α-syn$_{36-69}$ peptide (data not shown). Thus, it was confirmed in mice of the H2bxs haplotype that α-syn$_{36-69}$ does not possess a T cell epitope.

Recently, it was shown that calpain I cleaves the pathological form of α-syn generating a unique α-syn fragment. This α-syn fragment has an N-terminal sequence KAKEG (aa 10-14). KAKEG was tested as a B-cell epitope, a novel immunotherapy target for generation of antibodies inhibiting aberrant accumulation of α-syn in the central nervous system. A DNA vaccine encoding KAKEG fused to Multi-TEP platform was generated and C57Bl/6 mice were immunized using gene gun (biweekly, 3 times). Vaccinated mice generated strong antibody responses to KAKEG (FIG. 13A). In addition, this vaccine did not induce antibodies specific to full length α-syn, while this human protein was recognized by immune sera (positive control) collected from mice immunized with α-syn$_{36-69}$-MultiTEP (FIG. 13 B).

Immune sera from vaccinated mice was tested for recognition of pathological forms of α-syn in the human brain from the DLB case by IHC or IP/WB. Antibodies generated after immunizations with both α-syn$_{36-69}$-MultiTEP and KAKEG-MultiTEP, which did not recognize full length α-syn, showed positive staining of brain sections, an indication that these antibodies recognized the pathological form of α-syn. Control brain sections showed negative staining.

These experiments evidence that (i) epitope vaccine based on α-syn$_{36-69}$ fused with foreign Th cell epitopes (MultiTEP platform) induced high titers of anti-α-syn antibody; (ii)

antibodies generated by epitope vaccine are functional, since they bind to native α-syn ex vivo (iii) peptide α-syn$_{36-69}$ did not contain autoreactive Th cell epitopes, and hence can be used in an epitope vaccine; (iv) KAKEG-MultiTEP epitope vaccine induced strong antibody responses specific to KAKEG, but not to full length α-syn; and (v) antibodies specific to the KAKEG neoepitope recognized pathological form of α-syn and could also be used for the generation of a DNA epitope vaccine.

Example 7

Epitope Vaccine Targeting Pathological Tau Protein

This example describes the selection of tau epitope and generation and testing of an epitope vaccine targeting pathological tau.

Mapping of tau B cell epitopes. To map potentially important non-phosphorylated tau regions for the generation of therapeutic antibodies, anti-sera were obtained from tau transgenic mice rTg4510 (transgene is a human 4-repeat tau carrying P301L mutation controlled by cytomegalovirus minimal promoter and upstream tetracycline operator (tetO)) immunized with full length of tau (N2/4R). ELISA was used to detect binding of polyclonal sera to recombinant tau proteins from 1 aa to 50 aa, from 50 aa to 100aa, from 100aa to 150aa; from 150aa to 200aa, from 200aa to 250aa; from 250aa to 300aa; from 300aa to 350aa; from 350aa to 400aa; from 400aa to 441aa; thus we checked entire sequence of N2/4R molecule. Data demonstrated that anti-tau antibodies bind strongly to regions spanning aa 1 to 50 of tau protein and do not bind aa 50-100 or 250-300 (FIG. 14). Moderate binding was detected in wells coated with recombinant tau proteins spanning aa 150 to 200, 200 to 250; 350 to 400; and 400-441. Finally low binding was detected in wells coated with recombinant tau proteins spanning aa 100 to 150 and 300-350. These data provided the basis for selecting epitopes for generation of tau-targeting epitope vaccines important for active immunotherapy of subjects with taupathy. Tau region comprising 2-18 aa was selected for generation of epitope vaccine.

The aa2-18 region of tau is normally hidden due to folding of the protein, and it is exposed during aggregation of tau (Morfini G A, et al. *J Neurosci* 2009, 29:12776-12786; Horowitz P M, et al. *J Neurosci* 2004, 24:7895-7902). The aa2-18 region, also termed phosphatase-activating domain (PAD), plays a role in activation of a signaling cascade involving protein phosphatase I and glycogen synthase kinase 3, which leads to anterograde FAT inhibition. The exposure of PAD that is required for inhibition of FAT may be regulated by phosphorylation of PAD, as well as by N-terminal truncation of tau protein that occurs during formation of NFT. Phosphorylation of Y18 as well as truncation of N-terminal region of tau may remove a toxic region and have a protective role. Therefore, antibodies generated against this epitope may recognize pathologic, but not normal Tau. In such a case, the epitope vaccine may induce antibodies that will target very early stages of tauopathy.

To generate the epitope vaccine, tau2-18 epitope was fused with a foreign promiscuous Th epitope of TT (P30). B6SJL mice of H2bxs haplotype were immunized with a tau$_{2-18}$-P30 vaccine formulated in a strong Th1 adjuvant Quil A (the same as QS21). Both humoral (ELISA) and cellular (ELISPOT) immune responses were measured. Immunization induced high titers of tau$_{2-18}$-specific antibodies (FIG. 15A) that also recognized 4R/0N wild/type Tau, 4R/0N P301L Tau, and 4R/0N Tau with deleted region 19-29aa in ELISA (FIG. 15 B). Importantly, the epitope vaccine also induced a strong T cell response that was specific to P30, but not to tau$_{2-18}$ (FIG. 15 C). Thus, the tau$_{2-18}$-P30 vaccine formulated in QuilA adjuvant did not activate autoreactive Th cells while it generated strong non-self cellular immune responses and production of antibodies specific to various Tau proteins.

Example 8

Anti-Tau Antibodies Bind to Pathological Tau in Brains from AD Case

Figure 16:
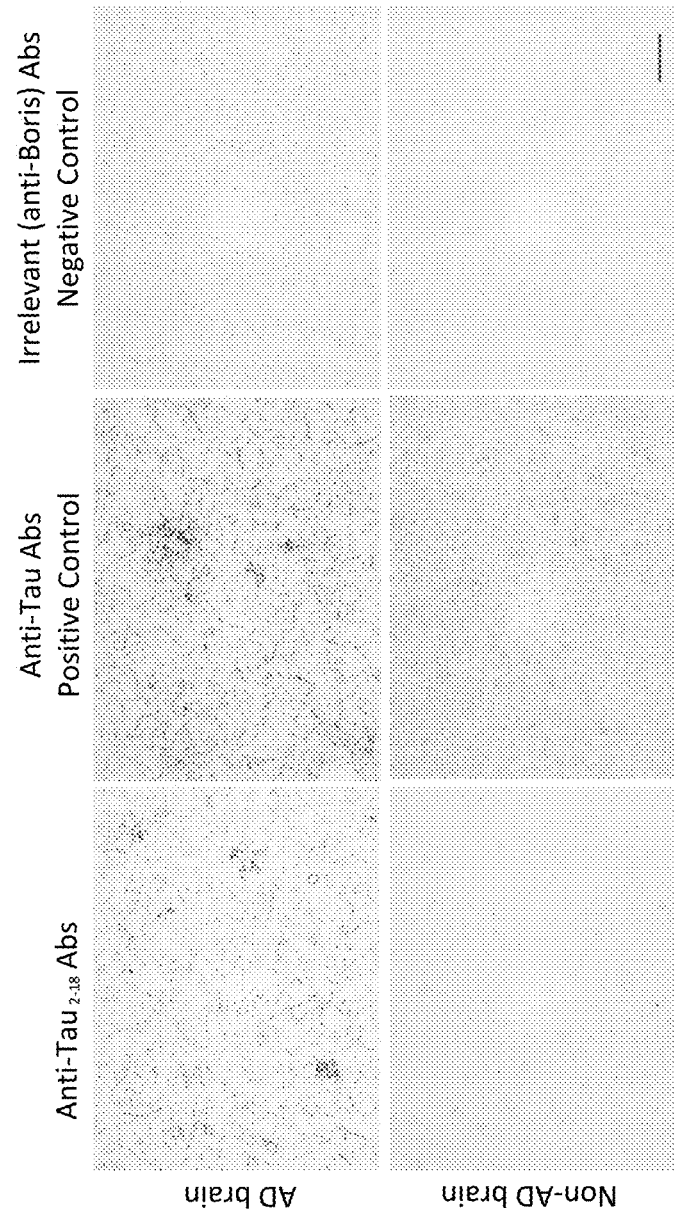

In this example we demonstrate the ability of anti-tau antibodies to bind pathological tau in brain sections from AD case. Sera from experimental mice immunized with the epitope vaccine and control animals immunized with irrelevant antigen were assayed on brain sections from AD and non-AD cases. Results showed that immune sera from experimental, but not control, mice at dilution 1:500 recognized NFT in the brain from AD case (Tangle stage V, Plaque stage C; FIG. 16). The same immune sera did not bind normal tau in a non-AD case. Therefore, tau epitope vaccine induced antibody responses specific to the pathological form of tau.

Example 9

Antibodies Block the Cell-Cell Propagation of Tau Aggregates

Figure 17A:
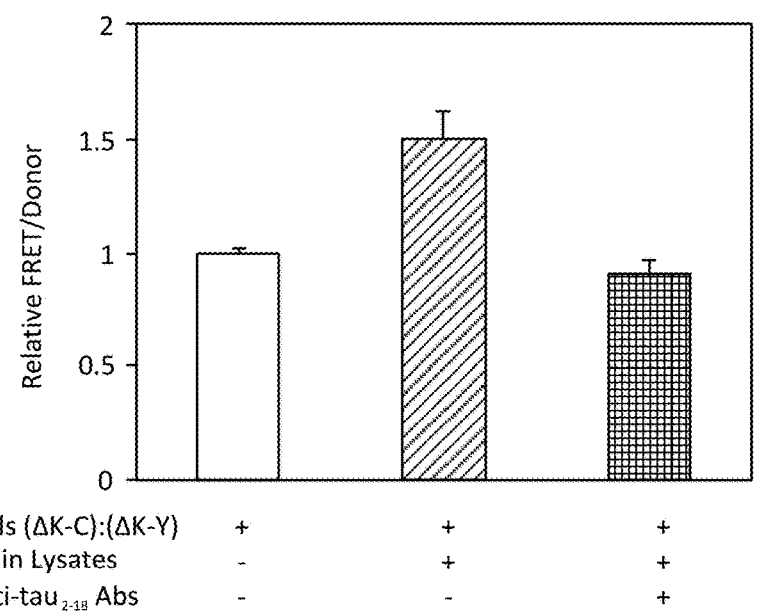
Figure 17B:
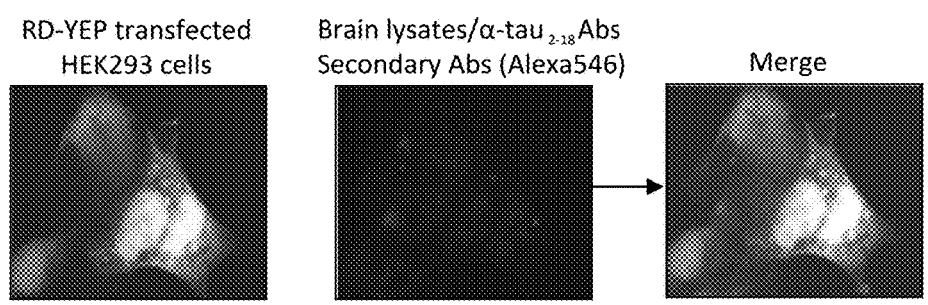

In this example, we demonstrate the therapeutic potential of anti-tau antibodies to block full-length tau aggregates from entering a cell and inducing aggregation of intracellular tau repeat domain (RD), the aggregation-prone core of Tau protein with mutation at position 280 (ΔK280) [RD (ΔK)] (Kfoury N, et al. *J Biol Chem*, 287:19440-19451, 2012). More specifically, a fluorescence resonance energy transfer (FRET) assay has been used for tracking the aggregation of the RD(ΔK)-CFP and RD(ΔK)-YFP proteins in HEK293 cells co-transfected with constructs expressing mentioned proteins that referred to (ΔK-C):(ΔK-Y) in FIG. 17. The more vigorous aggregation that was induced by adding brain lysate of P301S Tg mice containing full-length Tau aggregates to the culture of co-transfected cells increased FRET signal. Pre-treatment of brain-lysate with anti-tau$_{2-18}$ antibody trapped the tau aggregates on a surface of cells, inhibiting induction of (ΔK-C):(ΔK-Y) aggregation and decreased FRET signal to baseline level (FIG. 17A). In addition, using confocal microscopy, brain lysate/anti-tau$_{2-18}$ antibody complexes are shown to internalize into the RD-YFP transfected cells (FIG. 17B). Antibodies were not detected in non-transfected (NT) cells or in YFP cells in the absence of tau aggregates (data not shown). Importantly, when RD(ΔK) was replaced with a mutant form of tau containing two proline substitutions, I227P and I308P (termed PP), which inhibit β-sheet formation and fibrillization, no internalization of antibodies was observed (data not shown).

Figure 18A:
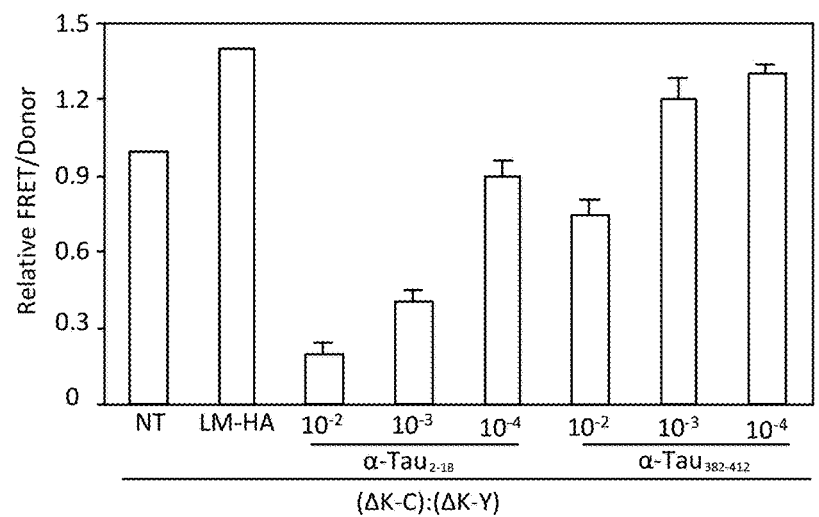
Figure 18B:
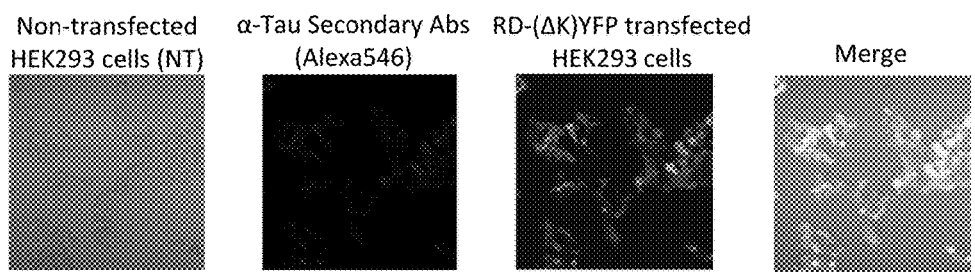

In another set of experiments the ability of anti-tau$_{2-18}$ antibodies to block trans-cellular movement of aggregated tau was tested. HEK293 cells were transfected with construct expressing hemagglutinin-tagged tau (RD) containing two disease-associated mutations that increase the capacity of protein to aggregate: P301L and V337M (LM) (LM-HA). When these cell populations were co-cultured with HEK293 cells expressing RD(ΔK)-CFP and RD(ΔK)-YFP proteins, trans-cellular propagation of LM-HA aggregates from donor cells (HEK293 cells transfected with LM-HA) induces aggregation of ΔK-C:ΔK-Y in recipient cells (HEK293 transfected with RD-CFP/RD-YFP) as detected by FRET between CFP and YFP. If anti-tau antibodies are added to this system and block propagation of tau, then FRET signal is decreased. Two antibodies specific to $tau_{2-18}$ and $Tau_{382-412}$ (generated in rats by immunization with $Tau_{382-412}$-PADRE) added to culture media at the indicated dilutions ($10^{-2}$, $10^{-3}$ and $10^{-4}$) during the 48 h co-culture period inhibited the cell-cell propagation of tau aggregates. Relative FRET across each group tested is shown in FIG. 18A. In addition, using confocal microscopy anti-tau antibodies are demonstrated to bind RD-YFP aggregates on a surface of transfected HEK293 cells (FIG. 18B).

These data suggest that α-$tau_{2-18}$ and α-$tau_{382-412}$ antibodies recognize a conformational antigenic determinant (mimotope/s) in aggregated RD. In addition, therapeutic anti-tau antibodies can be generated without using phosphorylated tau molecules or their derivatives (e.g. B cell epitopes) as an immunogen. Instead non-phosphorylated tau could be used for generation of therapeutic antibodies that will be safe to administrate to subjects with tauopathy, because such antibodies will not get inside the cells and inhibit function of normal tau molecules.

Example 10

Generation and Testing of Multivalent DNA Epitope Vaccine

Figure 19:
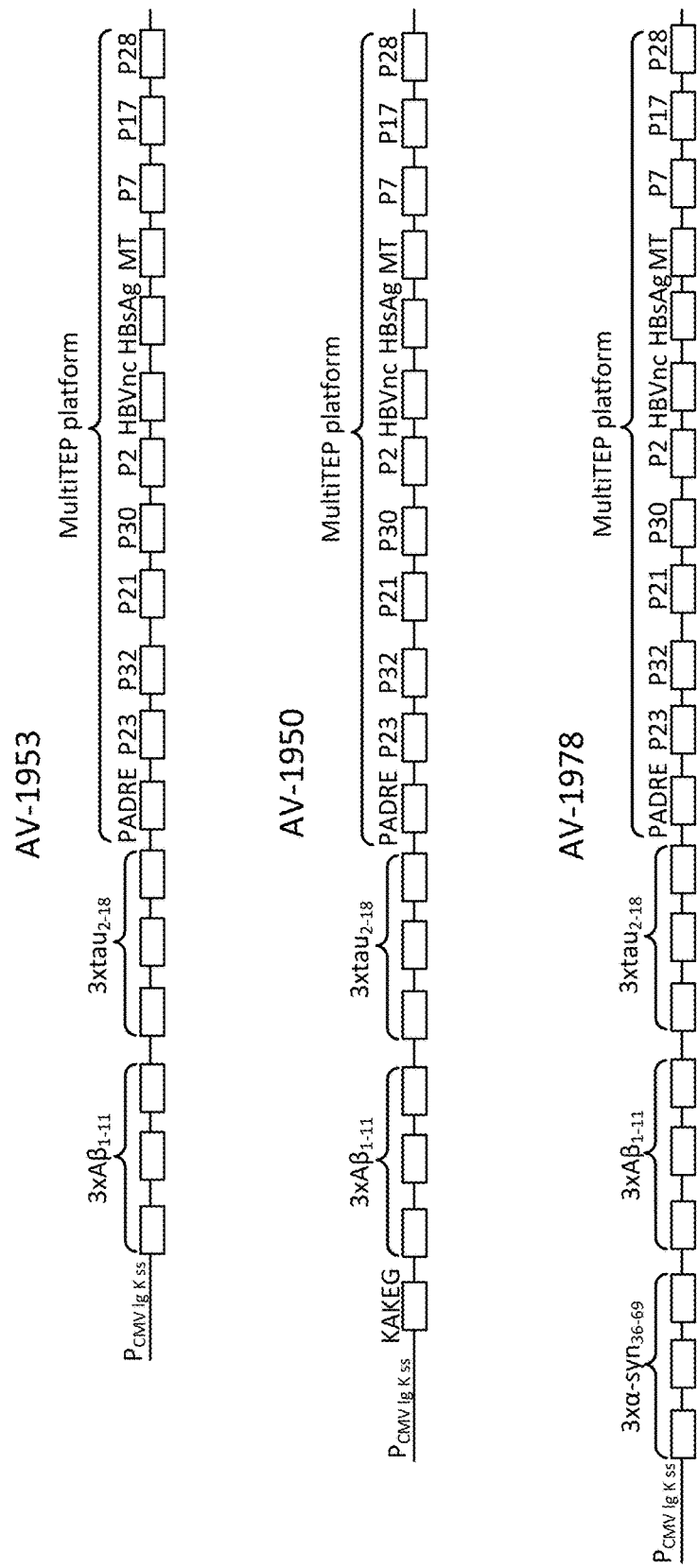

In this example, DNA epitope vaccines are generated that contain different combinations of B cell epitopes (FIG. 19) and tested. The vaccines generated contain (i) three copies of Aβ B cell epitope comprising aa 1-11 and three copies of Tau B cell epitope comprising aa 2-18; (ii) three copies of B cell epitope of α-syn comprising aa 36-69, three copies of Tau epitope comprising aa 2-18, and three copies of Aβ epitope comprising aa 1-11; and (iii) KAKEG epitope of α-syn, three copies of Tau epitope comprising aa 2-18, and three copies of Aβ epitope comprising aa 1-11. In all constructs B cell epitopes were fused to a string of foreign T cell epitopes. Each copy of B cell epitope and T cell epitope was separated by a GS small linker sequence (FIG. 19). The expression of the immunogen from plasmids containing these constructs was demonstrated using transiently transfected CHO cells (data not shown).

The DNA epitope vaccines were used for immunization of B6SJL mice (6 per group, 3 monthly injections) of H2bxs immune haplotype. Control animals were injected with an irrelevant DNA vaccine. Mice vaccinated with bivalent epitope vaccine (AV-1953) generated strong antibody responses to $Aβ_{42}$ and Tau protein (FIG. 20A). Mice vaccinated with trivalent epitope vaccines (AV-1950 and AV-1978) generated strong antibody responses to α-syn, $Aβ_{42}$ and Tau protein (FIG. 20B). Cellular immune responses were also measured and demonstrated that mice immunized with multivalent epitope vaccines induced robust T cell responses after re-stimulation with recombinant protein MultiTEP or a mix of peptides representing Th epitopes in a construct (FIG. 20C), but not with the α-syn, Tau, or $Aβ_{40}$.

It will be understood by persons of ordinary skill in the art that various changes in form and details can be made therein without departing from the spirit and scope of the invention.

The invention claimed is:

1. A composition, comprising at least one immunogen, wherein each at least one immunogen comprises a region A coupled to a region B; wherein region A comprises:
   (a) at least one Aβ B cell epitope in two or more copies, or
   (b) at least one Tau B cell epitope in two or more copies, or
   (c) at least one α-synuclein B cell epitope in two or more copies, or
   (d) a combination of at least one amyloid-β (Aβ) B cell epitope in two or more copies and at least one Tau B cell epitope in two or more copies, or
   (e) a combination of at least one amyloid-β (Aβ) B cell epitope in two or more copies and at least one α-synuclein B cell epitope in two or more copies, or
   (f) a combination of at least one Tau B cell epitope in two or more copies and at least one α-synuclein B cell epitope in two or more copies, or
   (g) a combination of at least one amyloid-β (Aβ)B cell epitope in two or more copies and at least one Tau B cell epitope in two or more copies and at least one α-synuclein B cell epitope in two or more copies, and region B comprises an amino acid sequence that comprises a plurality of foreign T helper cell (Th) epitopes and comprises at least one amino acid sequence of PADRE (SEQ ID NO: 36), tetanus toxin P7 (SEQ ID NO: 32), tetanus toxin P17 (SEQ ID NO: 31), or tetanus toxin P28 (SEQ ID NO: 30).

2. The composition of claim 1, wherein at least one immunogen comprises a linker domain coupling region A to region B.

3. The composition of claim 2, wherein the linker domain is selected from the group consisting of the amino acid sequence GS, GSGSG (SEQ ID NO: 37), YNGK (SEQ ID NO: 38) and A(EAAAK)nA (SEQ ID NO: 39), where n is 2-5.

4. The composition of claim 1, wherein region A is coupled to the N-terminus of region B or wherein region A is coupled to the C-terminus of region B.

5. The composition of claim 1, wherein the at least one Aβ B cell epitope is located within SEQ ID NO:1.

6. The composition of claim 5, wherein the Aβ B cell epitope comprises two or more copies of the amino acid sequence EFRH (SEQ ID NO: 41).

7. The composition of claim 1, wherein the at least one Tau B cell epitope is located within SEQ ID NO: 2.

8. The composition of claim 7, wherein the Tau B cell epitope comprises two or more copies of at least one amino acid sequence selected from the group consisting of:

```
                                                    (SEQ ID NO: 8)
AKAKTDHGAEIVYKSPVVSGDTSPRHLSNVSSTGSID, (SEQ ID NO: 9)
RSGYSSPGSPGTPGSRSR, (SEQ ID NO: 10)
NATRIPAKTPPAPKTPPSSGEPPKSGDRSGYSSPGS, (SEQ ID NO: 11)
GEPPKSGDRSGYSSPGSPGTPGSRSRTPSLPTPPTREPKK, (SEQ ID NO: 12)
KKVAVVRTPPKSPSS
and (SEQ ID NO: 13)
AEPRQEFEVMEDHAGTY.
```

9. The composition of claim 1, wherein the region B comprises the amino acid sequence

```
                                                    (SEQ ID NO: 45)
AKFVAAWTLKAAAGSVSIDKFRIFCKANPKGSLKFIIKRYTPNNEIDSGS

IREDNNITLKLDRCNNGSFNNFTVSFWLRVPKVSASHLEGSQYIKANSKF

IGITEGSPHHTALRQAILCWGELMTLAGSFFLLTRILTIPQSLDGSYSGP

LKAEIAQRLEDVGSNYSLDKIIVDYNLQSKITLPGSLINSTKIYSYFPSV

ISKVNQGSLEYIPEITLPVIAALSIAES.
```

10. A pharmaceutical composition comprising the composition of claim 1 and a pharmaceutically-acceptable excipient.

11. A composition comprising at least one nucleic acid molecule encoding an immunogen, wherein the immunogen comprises a region A coupled to a region B; wherein region A comprises:
   (a) at least one Aβ B cell epitope in two or more copies, or
   (b) at least one Tau B cell epitope in two or more copies or
   (c) at least one α-synuclein B cell epitope in two or more copies, or
   (d) a combination of at least one amyloid-β (Aβ) B cell epitope and at least one Tau B cell epitope, or
   (e) a combination of at least one amyloid-β (Aβ) B cell epitope in two or more copies and at least one α-synuclein B cell epitope in two or more copies, or
   (f) a combination of at least one Tau B cell epitope in two or more copies and at least one α-synuclein B cell epitope in two or more copies, or
   (g) a combination of at least one amyloid-β (Aβ) B cell epitope in two or more copies and at least one Tau B cell epitope in two or more copies and at least one α-synuclein B cell epitope in two or more copies, and region B comprises an amino acid sequence that comprises a plurality of foreign T helper cell (Th) epitopes and comprises at least one amino acid sequence of PADRE (SEQ ID NO: 36), tetanus toxin P7 (SEQ ID NO: 32), tetanus toxin P17 (SEQ ID NO: 31), or tetanus toxin P28 (SEQ ID NO: 30).

12. The composition of claim 11, wherein the nucleic acid molecule encodes a Tau B cell epitope comprising two or more copies of a sequence located within SEQ ID NO:5.

13. The composition of claim 11, wherein the nucleic acid molecule encodes an α-syn B cell epitope comprising two or more copies of a sequence located within SEQ ID NO:6.

14. A pharmaceutical composition comprising the composition of claim 11 and a pharmaceutically-acceptable excipient.

15. A method for generating an immune response in a subject against one or more of amyloid, tau or α-syn, comprising administering the composition of claim 10 to the subject.

16. The method of claim 15, wherein the subject is at risk of developing or has been diagnosed with Alzheimer's disease or one or more conditions associated with abnormal amyloid deposits, Tau deposits, and α-syn deposits.

17. A method for generating an immune response in a subject against one or more of amyloid, tau or α-syn, comprising administering the composition according to claim 14 to the subject.

18. The method of claim 17, wherein the subject is at risk of developing or has been diagnosed with Alzheimer's disease or one or more conditions associated with abnormal amyloid deposits, Tau deposits, and α-syn deposits.

19. The composition of claim 11, wherein the nucleic acid molecule encodes a Aβ B cell epitope comprising two or more copies of sequence EFRH (SEQ ID NO: 41).

20. The composition of claim 11, in which the region B comprises the amino acid sequence

```
                                        (SEQ ID NO: 45)
AKFVAAWTLKAAAGSVSIDKFRIFCKANPKGSLKFIIKRYTPNNEIDSGS

IREDNNITLKLDRCNNGSFNNFTVSFWLRVPKVSASHLEGSQYIKANSKF

IGITEGSPHHTALRQAILCWGELMTLAGSFFLLTRILTIPQSLDGSYSGP

LKAEIAQRLEDVGSNYSLDKIIVDYNLQSKITLPGSLINSTKIYSYFPSV

ISKVNQGSLEYIPEITLPVIAALSIAES.
```

21. A composition comprising at least one immunogen, wherein each at least one immunogen comprises a multi-TEP Th epitope that has the amino acid sequence

```
                                        (SEQ ID NO: 45)
AKFVAAWTLKAAAGSVSIDKFRIFCKANPKGSLKFIIKRYTPNNEIDSGS

IREDNNITLKLDRCNNGSFNNFTVSFWLRVPKVSASHLEGSQYIKANSKF

IGITEGSPHHTALRQAILCWGELMTLAGSFFLLTRILTIPQSLDGSYSGP

LKAEIAQRLEDVGSNYSLDKIIVDYNLQSKITLPGSLINSTKIYSYFPSV

ISKVNQGSLEYIPEITLPVIAALSIAES.
```

* * * * *

SEQUENCE LISTING

```
<160> NUMBER OF SEQ ID NOS: 46

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 776
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
```

```
            50                  55                  60
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Ala Gly Ile Gly Asp Thr Pro
                100                 105                 110

Ser Leu Glu Asp Glu Ala Ala Gly His Val Thr Gln Glu Pro Glu Ser
                115                 120                 125

Gly Lys Val Val Gln Glu Gly Phe Leu Arg Glu Pro Gly Pro Gly
                130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
                275                 280                 285

Val Gly Arg Ala Lys Gly Gln Asp Ala Pro Leu Glu Phe Thr Phe His
                290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser Lys Ser Lys Asp
                370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys Tyr Val Ser Ser Val Thr Ser Arg
                435                 440                 445

Thr Gly Ser Ser Gly Ala Lys Glu Met Lys Leu Lys Gly Ala Asp Gly
                450                 455                 460

Lys Thr Lys Ile Ala Thr Pro Arg Gly Ala Ala Pro Pro Gly Gln Lys
465                 470                 475                 480
```

```
Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
        515                 520                 525

Arg Ser Gly Tyr Ser Ser Pro Gly Ser Pro Gly Thr Pro Gly Ser Arg
    530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
        595                 600                 605

Lys Val Gln Ile Ile Asn Lys Lys Leu Asp Leu Ser Asn Val Gln Ser
    610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
            660                 665                 670

Glu Val Lys Ser Glu Lys Leu Asp Phe Lys Asp Arg Val Gln Ser Lys
        675                 680                 685

Ile Gly Ser Leu Asp Asn Ile Thr His Val Pro Gly Gly Gly Asn Lys
    690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
    770                 775

<210> SEQ ID NO 3
<211> LENGTH: 140
<212> TYPE: PRT
<213> ORGANISM: Homo sapiens

<400> SEQUENCE: 3

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
```

```
                65                  70                  75                  80
Thr Val Glu Gly Ala Gly Ser Ile Ala Ala Ala Thr Gly Phe Val Lys
                    85                  90                  95
Lys Asp Gln Leu Gly Lys Asn Glu Glu Gly Ala Pro Gln Glu Gly Ile
                    100                 105                 110
Leu Glu Asp Met Pro Val Asp Pro Asp Asn Glu Ala Tyr Glu Met Pro
            115                 120                 125
Ser Glu Glu Gly Tyr Gln Asp Tyr Glu Pro Glu Ala
        130                 135                 140

<210> SEQ ID NO 4
<211> LENGTH: 126
<212> TYPE: DNA
<213> ORGANISM: Homo sapiens

<400> SEQUENCE: 4
gatgcagaat tccgacatga ctcaggatat gaagttcatc atcaaaaatt ggtgttcttt    60
gcagaagatg tgggttcaaa caaggtgca atcattggac tcatggtggg cggtgttgtc   120
atagcg                                                               126

<210> SEQ ID NO 5
<211> LENGTH: 2331
<212> TYPE: DNA
<213> ORGANISM: Homo sapiens

<400> SEQUENCE: 5
atggctgagc ccgccagga gttcgaagtg atggaagatc acgctgggac gtacgggttg     60
ggggacagga agatcagggg gggctacacc atgcaccaag accaagaggg tgacacggac   120
gctggcctga agaatctcc cctgcagacc cccactgagg acggatctga ggaaccgggc   180
tctgaaacct ctgatgctaa gagcactcca acagcggaag atgtgacagc accttagtg   240 gatgagggag ctcccggcaa gcaggctgcc gcgcagcccc acgcgagat cccagaagga   300 accacagctg aagaagcagg cattggagac ccccagcc tggaagacga agctgctggt   360
cacgtgaccc aagagcctga aagtgggtaag gtggtccagg aaggcttcct ccgagagcca   420 ggcccccccag gtctgagcca ccagctcatg tccggcatgc ctgggctcc cctcctgcct   480 gagggccccca gagaggccac acgccaacct tcggggacag acctgaggga cacagagggc   540
ggccgccacg ccctgagct gctcaagcac cagcttctag agacctgca ccaggagggg   600 ccgccgctga ggggggcagg gggcaaagag aggccgggga gcaaggagga ggtggatgaa   660
gaccgcgacg tcgatgagtc ctccccccaa gactcccctc cctccaaggc ctccccagcc   720
caagatgggc ggcctcccca gacagccgcc agagaagcca ccagcatccc aggcttccca   780
gcggagggtg ccatcccccc tccctgtggat ttcctctcca agtttccac agagatccca   840 gcctcagagc ccgacgggcc cagtgtaggg cgggccaaag gcaggatgc cccctggag   900 ttcacgtttc acgtggaaat cacacccaac gtgcagaagg agcaggcgca ctcggaggag   960
catttgggaa gggctgcatt tccaggggcc cctggagagg ggccagaggc ccggggcccc  1020
tctttgggag aggacacaaa agaggctgac cttccagagc cctctgaaaa gcagcctgct  1080
gctgctccgc gggggaagcc cgtcagccgg gtccctcaac tcaaagctcg catggtcagt  1140
aaaagcaaag acgggactgg aagcgatgac aaaaaagcca agacatccac acgttcctct  1200
gctaaaacct tgaaaaatag gccttgcctt agccccaaac ccccactcc tggtagctca  1260 gaccctctga tccaaccctc cagccctgct gtgtgcccag agccaccttc ctctcctaaa  1320
```

```
tacgtctctt ctgtcacttc ccgaactggc agttctggag caaaggagat gaaactcaag    1380
ggggctgatg gtaaaacgaa gatcgccaca ccgcggggag cagcccctcc aggccagaag    1440
ggccaggcca acgccaccag gattccagca aaaccccgc ccgctccaaa gacaccaccc     1500
agctctgcga ctaagcaagt ccagagaaga ccaccccctg cagggcccag atctgagaga    1560
ggtgaacctc caaaatcagg ggatcgcagc ggctacagca gccccggctc cccaggcact    1620
cccggcagcc gctcccgcac cccgtccctt ccaaccccac ccaccgggga gcccaagaag    1680
gtggcagtgg tccgtactcc acccaagtcg ccgtcttccg ccaagagccg cctgcagaca    1740
gcccccgtgc ccatgccaga cctgaagaat gtcaagtcca agatcggctc cactgagaac    1800
ctgaagcacc agccgggagg cgggaaggtg cagataatta ataagaagct ggatcttagc    1860
aacgtccagt ccaagtgtgg ctcaaaggat aatatcaaac acgtcccggg aggcggcagt    1920
gtgcaaatag tctacaaacc agttgacctg agcaaggtga cctccaagtg tggctcatta    1980
ggcaacatcc atcataaacc aggaggtggc caggtggaag taaaatctga gaagcttgac    2040
ttcaaggaca gagtccagtc gaagattggg tccctggaca atatcaccca cgtccctggc    2100
ggaggaaata aaaagattga aacccacaag ctgaccttcc gcgagaacgc caaagccaag    2160
acagaccacg gggcggagat cgtgtacaag tcgccagtgg tgtctgggga cacgtctcca    2220
cggcatctca gcaatgtctc ctccaccggc agcatcgaca tggtagactc gccccagctc    2280
gccacgctag ctgacgaggt gtctgcctcc ctggccaagc agggtttgtg a             2331

<210> SEQ ID NO 6
<211> LENGTH: 423
<212> TYPE: DNA
<213> ORGANISM: Homo sapiens

<400> SEQUENCE: 6
atggatgtat tcatgaaagg actttcaaag gccaaggagg gagttgtggc tgctgctgag     60
aaaaccaaac agggtgtggc agaagcagca ggaaagacaa agagggtgt tctctatgta     120 ggctccaaaa ccaaggaggg agtggtgcat ggtgtggcaa cagtggctga aagaccaaa      180 gagcaagtga caaatgttgg aggagcagtg gtgacgggtg tgacagcagt agcccagaag     240
acagtggagg gagcagggag cattgcagca gccactggct ttgtcaaaaa ggaccagttg     300
ggcaagaatg aagaaggagc cccacaggaa ggaattctgg aagatatgcc tgtggatcct     360
gacaatgagg cttatgaaat gccttctgag gaagggtatc aagactacga acctgaagcc     420
taa                                                                   423

<210> SEQ ID NO 7
<211> LENGTH: 6
<212> TYPE: PRT
<213> ORGANISM: Homo sapiens

<400> SEQUENCE: 7

Asp Ala Glu Phe Arg His
1               5

<210> SEQ ID NO 8
<211> LENGTH: 37
<212> TYPE: PRT
<213> ORGANISM: Homo sapiens

<400> SEQUENCE: 8

Ala Lys Ala Lys Thr Asp His Gly Ala Glu Ile Val Tyr Lys Ser Pro
```

```
  1               5                  10                 15
Val Val Ser Gly Asp Thr Ser Pro Arg His Leu Ser Asn Val Ser Ser
              20                 25                 30

Thr Gly Ser Ile Asp
            35

<210> SEQ ID NO 9
<211> LENGTH: 18
<212> TYPE: PRT
<213> ORGANISM: Homo sapiens

<400> SEQUENCE: 9

Arg Ser Gly Tyr Ser Ser Pro Gly Ser Pro Gly Thr Pro Gly Ser Arg
  1               5                  10                 15

Ser Arg

<210> SEQ ID NO 10
<211> LENGTH: 36
<212> TYPE: PRT
<213> ORGANISM: Homo sapiens

<400> SEQUENCE: 10

Asn Ala Thr Arg Ile Pro Ala Lys Thr Pro Ala Pro Lys Thr Pro
  1               5                  10                 15

Pro Ser Ser Gly Glu Pro Pro Lys Ser Gly Asp Arg Ser Gly Tyr Ser
              20                 25                 30

Ser Pro Gly Ser
            35

<210> SEQ ID NO 11
<211> LENGTH: 40
<212> TYPE: PRT
<213> ORGANISM: Homo sapiens

<400> SEQUENCE: 11

Gly Glu Pro Pro Lys Ser Gly Asp Arg Ser Gly Tyr Ser Ser Pro Gly
  1               5                  10                 15

Ser Pro Gly Thr Pro Gly Ser Arg Ser Arg Thr Pro Ser Leu Pro Thr
              20                 25                 30

Pro Pro Thr Arg Glu Pro Lys Lys
            35                 40

<210> SEQ ID NO 12
<211> LENGTH: 15
<212> TYPE: PRT
<213> ORGANISM: Homo sapiens

<400> SEQUENCE: 12

Lys Lys Val Ala Val Val Arg Thr Pro Pro Lys Ser Pro Ser Ser
  1               5                  10                 15

<210> SEQ ID NO 13
<211> LENGTH: 17
<212> TYPE: PRT
<213> ORGANISM: Homo sapiens

<400> SEQUENCE: 13

Ala Glu Pro Arg Gln Glu Phe Glu Val Met Glu Asp His Ala Gly Thr
  1               5                  10                 15

Tyr
```

-continued

<210> SEQ ID NO 14
<211> LENGTH: 49
<212> TYPE: PRT
<213> ORGANISM: Homo sapiens

<400> SEQUENCE: 14

Lys Thr Lys Glu Gly Val Leu Tyr Val Gly Ser Lys Thr Lys Glu Gly
1               5                   10                  15

Val Val His Gly Val Ala Thr Val Ala Glu Lys Thr Lys Glu Gln Val
            20                  25                  30

Thr Asn Val Gly Gly Ala Val Val Thr Gly Val Thr Ala Val Ala Gln
        35                  40                  45

Lys

<210> SEQ ID NO 15
<211> LENGTH: 15
<212> TYPE: PRT
<213> ORGANISM: Homo sapiens

<400> SEQUENCE: 15

Ala Gly Ser Ile Ala Ala Ala Thr Gly Phe Val Lys Lys Asp Gln
1               5                   10                  15

<210> SEQ ID NO 16
<211> LENGTH: 18
<212> TYPE: PRT
<213> ORGANISM: Homo sapiens

<400> SEQUENCE: 16

Gln Glu Gly Ile Leu Glu Asp Met Pro Val Asp Pro Asp Asn Glu Ala
1               5                   10                  15

Tyr Glu

<210> SEQ ID NO 17
<211> LENGTH: 15
<212> TYPE: PRT
<213> ORGANISM: Homo sapiens

<400> SEQUENCE: 17

Glu Met Pro Ser Glu Glu Gly Tyr Gln Asp Tyr Glu Pro Glu Ala
1               5                   10                  15

<210> SEQ ID NO 18
<211> LENGTH: 5
<212> TYPE: PRT
<213> ORGANISM: Homo sapiens

<400> SEQUENCE: 18

Lys Ala Lys Glu Gly
1               5

<210> SEQ ID NO 19
<211> LENGTH: 15
<212> TYPE: PRT
<213> ORGANISM: Homo sapiens

<400> SEQUENCE: 19

Glu Met Pro Ser Glu Glu Gly Tyr Gln Asp Tyr Glu Pro Glu Ala
1               5                   10                  15

<210> SEQ ID NO 20
<211> LENGTH: 15

```
<212> TYPE: PRT
<213> ORGANISM: Homo sapiens

<400> SEQUENCE: 20

Val Phe Phe Ala Glu Asp Val Gly Ser Asn Lys Gly Ala Ile Ile
1               5                   10                  15

<210> SEQ ID NO 21
<211> LENGTH: 20
<212> TYPE: PRT
<213> ORGANISM: Homo sapiens

<400> SEQUENCE: 21

Gln Lys Leu Val Phe Phe Ala Glu Asp Val Gly Ser Asn Lys Gly Ala
1               5                   10                  15

Ile Ile Gly Leu
            20

<210> SEQ ID NO 22
<211> LENGTH: 14
<212> TYPE: PRT
<213> ORGANISM: Homo sapiens

<400> SEQUENCE: 22

Leu Val Phe Phe Ala Glu Asp Val Gly Ser Asn Lys Gly Ala
1               5                   10

<210> SEQ ID NO 23
<211> LENGTH: 15
<212> TYPE: PRT
<213> ORGANISM: Homo sapiens

<400> SEQUENCE: 23

Gln Lys Leu Val Phe Phe Ala Glu Asp Val Gly Ser Asn Lys Gly
1               5                   10                  15

<210> SEQ ID NO 24
<211> LENGTH: 18
<212> TYPE: PRT
<213> ORGANISM: Homo sapiens

<400> SEQUENCE: 24

Gly Ser Asn Lys Gly Ala Ile Ile Gly Leu Met Val Gly Gly Val Val
1               5                   10                  15

Ile Ala

<210> SEQ ID NO 25
<211> LENGTH: 15
<212> TYPE: PRT
<213> ORGANISM: Clostridium tetani

<400> SEQUENCE: 25

Val Ser Ile Asp Lys Phe Arg Ile Phe Cys Lys Ala Asn Pro Lys
1               5                   10                  15

<210> SEQ ID NO 26
<211> LENGTH: 16
<212> TYPE: PRT
<213> ORGANISM: Clostridium tetani

<400> SEQUENCE: 26

Leu Lys Phe Ile Ile Lys Arg Tyr Thr Pro Asn Asn Glu Ile Asp Ser
1               5                   10                  15
```

```
<210> SEQ ID NO 27
<211> LENGTH: 16
<212> TYPE: PRT
<213> ORGANISM: Clostridium tetani

<400> SEQUENCE: 27

Ile Arg Glu Asp Asn Asn Ile Thr Leu Lys Leu Asp Arg Cys Asn Asn
1               5                   10                  15

<210> SEQ ID NO 28
<211> LENGTH: 21
<212> TYPE: PRT
<213> ORGANISM: Clostridium tetani

<400> SEQUENCE: 28

Phe Asn Asn Phe Thr Val Ser Phe Trp Leu Arg Val Pro Lys Val Ser
1               5                   10                  15

Ala Ser His Leu Glu
            20

<210> SEQ ID NO 29
<211> LENGTH: 14
<212> TYPE: PRT
<213> ORGANISM: Clostridium tetani

<400> SEQUENCE: 29

Gln Tyr Ile Lys Ala Asn Ser Lys Phe Ile Gly Ile Thr Glu
1               5                   10

<210> SEQ ID NO 30
<211> LENGTH: 20
<212> TYPE: PRT
<213> ORGANISM: Clostridium tetani

<400> SEQUENCE: 30

Leu Glu Tyr Ile Pro Glu Ile Thr Leu Pro Val Ile Ala Ala Leu Ser
1               5                   10                  15

Ile Ala Glu Ser
            20

<210> SEQ ID NO 31
<211> LENGTH: 20
<212> TYPE: PRT
<213> ORGANISM: Clostridium tetani

<400> SEQUENCE: 31

Leu Ile Asn Ser Thr Lys Ile Tyr Ser Tyr Phe Pro Ser Val Ile Ser
1               5                   10                  15

Lys Val Asn Gln
            20

<210> SEQ ID NO 32
<211> LENGTH: 20
<212> TYPE: PRT
<213> ORGANISM: Clostridium tetani

<400> SEQUENCE: 32

Asn Tyr Ser Leu Asp Lys Ile Ile Val Asp Tyr Asn Leu Gln Ser Lys
1               5                   10                  15

Ile Thr Leu Pro
            20
```

```
<210> SEQ ID NO 33
<211> LENGTH: 20
<212> TYPE: PRT
<213> ORGANISM: Hepatitis B virus

<400> SEQUENCE: 33

Pro His His Thr Ala Leu Arg Gln Ala Ile Leu Cys Trp Gly Glu Leu
1               5                   10                  15

Met Thr Leu Ala
            20

<210> SEQ ID NO 34
<211> LENGTH: 15
<212> TYPE: PRT
<213> ORGANISM: Hepatitis B virus

<400> SEQUENCE: 34

Phe Phe Leu Leu Thr Arg Ile Leu Thr Ile Pro Gln Ser Leu Asp
1               5                   10                  15

<210> SEQ ID NO 35
<211> LENGTH: 16
<212> TYPE: PRT
<213> ORGANISM: Influenza B virus

<400> SEQUENCE: 35

Tyr Ser Gly Pro Leu Lys Ala Glu Ile Ala Gln Arg Leu Glu Asp Val
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: synthesized fusion protein

<400> SEQUENCE: 36

Ala Lys Phe Val Ala Ala Trp Thr Leu Lys Ala Ala Ala
1               5                   10

<210> SEQ ID NO 37
<211> LENGTH: 5
<212> TYPE: PRT
<213> ORGANISM: Artificial Sequence
<220> FEATURE:
<223> OTHER INFORMATION: synthesized fusion fragments

<400> SEQUENCE: 37

Gly Ser Gly Ser Gly
1               5

<210> SEQ ID NO 38
<211> LENGTH: 4
<212> TYPE: PRT
<213> ORGANISM: Artificial Sequence
<220> FEATURE:
<223> OTHER INFORMATION: synthesized fusion fragments

<400> SEQUENCE: 38

Tyr Asn Gly Lys
1

<210> SEQ ID NO 39
<211> LENGTH: 7
<212> TYPE: PRT
<213> ORGANISM: Artificial Sequence
```

```
<220> FEATURE:
<223> OTHER INFORMATION: synthesized protein fragment with the sequence
      EAAAK repeated n times, where n=2,3,4 or 5

<400> SEQUENCE: 39

Ala Glu Ala Ala Ala Lys Ala
1               5

<210> SEQ ID NO 40
<211> LENGTH: 13
<212> TYPE: PRT
<213> ORGANISM: Artificial Sequence
<220> FEATURE:
<223> OTHER INFORMATION: modified sequence
<220> FEATURE:
<221> NAME/KEY: MISC_FEATURE
<222> LOCATION: (1)..(1)
<223> OTHER INFORMATION: D-alanine
<220> FEATURE:
<221> NAME/KEY: MISC_FEATURE
<222> LOCATION: (3)..(3)
<223> OTHER INFORMATION: L-cyclohexylalanine
<220> FEATURE:
<221> NAME/KEY: MISC_FEATURE
<222> LOCATION: (3)..(3)
<220> FEATURE:
<221> NAME/KEY: MISC_FEATURE
<222> LOCATION: (13)..(13)
<223> OTHER INFORMATION: D-alanine

<400> SEQUENCE: 40

Xaa Lys Xaa Val Ala Ala Trp Thr Leu Lys Ala Ala Xaa
1               5                   10

<210> SEQ ID NO 41
<211> LENGTH: 4
<212> TYPE: PRT
<213> ORGANISM: Homo sapiens

<400> SEQUENCE: 41

Glu Phe Arg His
1

<210> SEQ ID NO 42
<211> LENGTH: 20
<212> TYPE: PRT
<213> ORGANISM: Homo sapiens

<400> SEQUENCE: 42

Gly Lys Thr Lys Glu Gly Val Leu Tyr Val Gly Ser Lys Thr Lys Glu
1               5                   10                  15

Gly Val Val His
            20

<210> SEQ ID NO 43
<211> LENGTH: 24
<212> TYPE: PRT
<213> ORGANISM: Homo sapiens

<400> SEQUENCE: 43

Glu Gly Val Val His Gly Val Ala Thr Val Ala Glu Lys Thr Lys Glu
1               5                   10                  15

Gln Val Thr Asn Val Gly Gly Ala
            20

<210> SEQ ID NO 44
<211> LENGTH: 20
```

<212> TYPE: PRT
<213> ORGANISM: Homo sapiens

<400> SEQUENCE: 44

Glu Gln Val Thr Asn Val Gly Gly Ala Val Val Thr Gly Val Thr Ala
1               5                   10                  15

Val Ala Gln Lys
            20

<210> SEQ ID NO 45
<211> LENGTH: 228
<212> TYPE: PRT
<213> ORGANISM: artificial
<220> FEATURE:
<223> OTHER INFORMATION: recombinant artificial protein

<400> SEQUENCE: 45

Ala Lys Phe Val Ala Ala Trp Thr Leu Lys Ala Ala Gly Ser Val
1               5                   10                  15

Ser Ile Asp Lys Phe Arg Ile Phe Cys Lys Ala Asn Pro Lys Gly Ser
                20                  25                  30

Leu Lys Phe Ile Ile Lys Arg Tyr Thr Pro Asn Asn Glu Ile Asp Ser
            35                  40                  45

Gly Ser Ile Arg Glu Asp Asn Asn Ile Thr Leu Lys Leu Asp Arg Cys
50                  55                  60

Asn Asn Gly Ser Phe Asn Phe Thr Val Ser Phe Trp Leu Arg Val
65                  70                  75                  80

Pro Lys Val Ser Ala Ser His Leu Glu Gly Ser Gln Tyr Ile Lys Ala
                85                  90                  95

Asn Ser Lys Phe Ile Gly Ile Thr Glu Gly Ser Pro His His Thr Ala
            100                 105                 110

Leu Arg Gln Ala Ile Leu Cys Trp Gly Glu Leu Met Thr Leu Ala Gly
        115                 120                 125

Ser Phe Phe Leu Leu Thr Arg Ile Leu Thr Ile Pro Gln Ser Leu Asp
130                 135                 140

Gly Ser Tyr Ser Gly Pro Leu Lys Ala Glu Ile Ala Gln Arg Leu Glu
145                 150                 155                 160

Asp Val Gly Ser Asn Tyr Ser Leu Asp Lys Ile Ile Val Asp Tyr Asn
                165                 170                 175

Leu Gln Ser Lys Ile Thr Leu Pro Gly Ser Leu Ile Asn Ser Thr Lys
            180                 185                 190

Ile Tyr Ser Tyr Phe Pro Ser Val Ile Ser Lys Val Asn Gln Gly Ser
        195                 200                 205

Leu Glu Tyr Ile Pro Glu Ile Thr Leu Pro Val Ile Ala Ala Leu Ser
210                 215                 220

Ile Ala Glu Ser
225

<210> SEQ ID NO 46
<211> LENGTH: 34
<212> TYPE: PRT
<213> ORGANISM: Homo sapiens

```
<400> SEQUENCE: 46

Gly Val Leu Tyr Val Gly Ser Lys Thr Lys Glu Gly Val Val His Gly
1               5                   10                  15

Val Ala Thr Val Ala Glu Lys Thr Lys Glu Gln Val Thr Asn Val Gly
            20                  25                  30

Gly Ala
```